United States Patent
Li et al.

(10) Patent No.: US 12,209,141 B2
(45) Date of Patent: Jan. 28, 2025

(54) DIPEPTIDE COMPOUNDS AND USES THEREOF

(71) Applicant: HUAHAI US INC., Somerset, NJ (US)

(72) Inventors: Min Li, Ringoes, NJ (US); Yu Huang, Shanghai (CN)

(73) Assignee: SHANGHAI SYNERGY PHARMACEUTICAL SCIENCES, LTD., Shanghai (CN)

(*) Notice: Subject to any disclaimer, the term of this patent is extended or adjusted under 35 U.S.C. 154(b) by 606 days.

(21) Appl. No.: 17/289,379

(22) PCT Filed: Oct. 25, 2019

(86) PCT No.: PCT/US2019/057985
§ 371 (c)(1),
(2) Date: Apr. 28, 2021

(87) PCT Pub. No.: WO2020/092139
PCT Pub. Date: May 7, 2020

(65) Prior Publication Data
US 2021/0395299 A1 Dec. 23, 2021

Related U.S. Application Data

(60) Provisional application No. 62/751,984, filed on Oct. 29, 2018.

(51) Int. Cl.
| | |
|---|---|
| C07K 5/062 | (2006.01) |
| A61K 47/54 | (2017.01) |
| A61P 7/02 | (2006.01) |
| A61K 38/00 | (2006.01) |

(52) U.S. Cl.
CPC ........ C07K 5/06043 (2013.01); A61K 47/545 (2017.08); A61P 7/02 (2018.01); A61K 38/00 (2013.01)

(58) Field of Classification Search
CPC .. C07K 5/06043; A61K 47/545; A61K 38/00; A61P 7/02
USPC ........................................................ 514/14.9
See application file for complete search history.

(56) References Cited

U.S. PATENT DOCUMENTS

| | | |
|---|---|---|
| 6,288,077 B1 | 9/2001 | De Nanteuil et al. |
| 6,774,110 B2 | 8/2004 | Lee et al. |
| 2002/0169113 A1 | 11/2002 | Lee et al. |
| 2005/0085517 A1 | 4/2005 | De Nanteuil et al. |
| 2013/0296245 A1* | 11/2013 | Li ............... C07K 5/06043 |
| | | 546/225 |

FOREIGN PATENT DOCUMENTS

| | | |
|---|---|---|
| CN | 102464701 | 5/2012 |
| EP | 1 050 534 A1 | 11/2000 |
| EP | 2 639 230 A1 | 9/2013 |
| EP | 2639230 | 9/2013 |
| JP | 2000344745 | 12/2000 |
| JP | 2005517734 | 6/2005 |
| JP | 2006249098 | 9/2006 |
| JP | 2013543850 | 12/2013 |

OTHER PUBLICATIONS

Extended European Search Report issued for corresponding European Application No. 19877652.8, dated Jul. 11, 2022, 8 pages.

* cited by examiner

Primary Examiner — Jeanette M Lieb
Assistant Examiner — Erinne R Dabkowski
(74) Attorney, Agent, or Firm — NIXON & VANDERHYE, PC

(57) ABSTRACT

Provided herein are novel compounds of Formula I, or a pharmaceutically acceptable salt thereof or pharmaceutical compositions comprising the same. Also provided are methods of preparing the compounds of Formula I, or pharmaceutically acceptable salt thereof. Further provided are methods of using the novel compounds of Formula I, or a pharmaceutically acceptable salt thereof, for example, for inhibiting thrombin and/or for the use in the prevention and/or treatment of thrombin-mediated and thrombin-related diseases.

Formula I

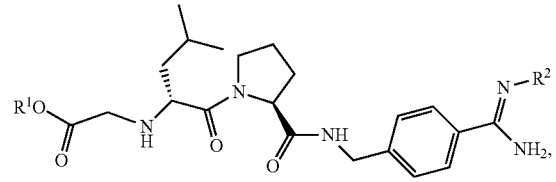

5 Claims, No Drawings

DIPEPTIDE COMPOUNDS AND USES THEREOF

CROSS-REFERENCE TO RELATED APPLICATIONS

This application is the U.S. National Phase of PCT Application No. PCT/US2019/057985, filed Oct. 25, 2019, which claims benefit to U.S. Provisional Application No. 62/751,984, filed Oct. 29, 2018, the contents of each of which are herein incorporated by reference in their entireties.

BACKGROUND OF THE INVENTION

Field of the Invention

The present invention relates to novel disubstituted dipeptide pharmaceutical compounds, and salts thereof, particularly physiologically acceptable salts formed with organic or inorganic acids. Specifically, the present invention relates to a process for the preparation of such compounds, to the uses thereof for the prevention and treatment of thromboembolic diseases, and to pharmaceutical compositions containing them. The novel compounds of the present invention are useful as competitive inhibitors of tryptase-like serine proteases, particularly thrombin.

Background Art

The mortality rate of cardiovascular and cerebrovascular diseases in the world has been the second in the world, and thromboembolism is the main cause of high incidence of cardiovascular and cerebrovascular diseases. Especially with the changes in people's lifestyles and the aging of the population, the incidence of such diseases is on the rise. This makes it particularly urgent to explore and research drugs that effectively prevent and treat such diseases, both in clinical applications and in basic research.

Thrombosis is caused by a series of complex reactions that cause blood clotting. The normal coagulation cascade of living organisms can quickly and securely seal the damaged vessel wall, thus avoiding bleeding. Uncontrolled activation of coagulation system or lack of inhibition mechanisms during activation processes may result in a variety of related diseases or complications, for example: Deep Venous Thrombosis (DVT), Pulmonary Embolism (PE), Myocardial Infarction or Cerebral Infarction, Atrial Fibrillation, and the like.

There are two main types of oral anticoagulant drugs currently on the market: direct thrombin inhibitors and direct factor Xa inhibitors. Blood coagulation is the result of a complex series of enzymes, a key step in which endogenous and exogenous chain reactions lead to the activation of prothrombin to thrombin by multiple amplification steps. Thrombin is a tryptase-like serine protease that acts to hydrolyze fibrinogen to form insoluble fibrous aggregates, triggering coagulation and platelet aggregation, and plays a key role in the blood coagulation cascade. Therefore, inhibition of thrombin activity can block the formation of thrombus. Dabigatran etexilate, marketed in 2008, is currently the only orally effective direct thrombin inhibitor. Clinically, dabigatran etexilate can be used as an alternative to warfarin, and as one of the first choices for preventing stroke and systemic embolism in patients with nonvalvular atrial fibrillation (NVAF) and preventing postoperative deep vein thrombosis. However, dabigatran etexilate has a low oral bioavailability and is mainly excreted by the kidneys, so it still has its defects. To date, convenient treatment of thrombosis, effective selectivity, and oral bioavailable thrombin inhibitors have represented an attractive option.

BRIEF SUMMARY OF THE INVENTION

In various embodiments, the present invention provides a novel orally administrable series of compounds which have significant antithrombotic effects and which have good stability, solubility, pharmacokinetic properties, low toxicity or long-acting effects. In some embodiments, methods of preparation, methods of use, for example, for inhibiting thrombin and/or for treating or preventing a thrombin-mediated and/or thrombin-related diseases are also provided.

In some embodiments, the present invention provides the following exemplary embodiments, Embodiments 1-32:

Embodiment 1

A compound of Formula I, or a pharmaceutically acceptable salt thereof,

Formula I

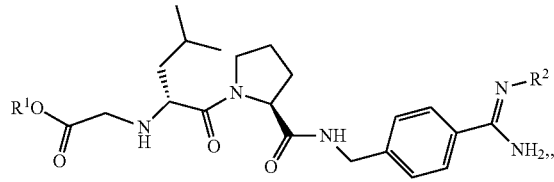

wherein $R^1$ is hydrogen, an optionally substituted alkyl, an optionally substituted alkenyl, or an optionally substituted alkynyl, and $R^2$ is hydrogen,

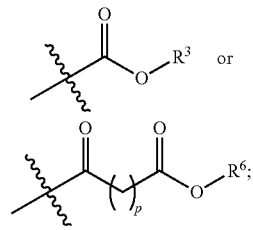

wherein p is an integer ranging from 1-6, and $R^3$ is an optionally substituted alkyl (e.g., an optionally substituted aralkyl or optionally substituted heteroaralkyl), an optionally substituted alkenyl, an optionally substituted alkynyl, an optionally substituted cycloalkyl, an optionally substituted heterocyclyl, an optionally substituted aryl, or an optionally substituted heteroaryl; and $R^6$ is hydrogen, an optionally substituted alkyl (e.g., an optionally substituted aralkyl or optionally substituted heteroaralkyl), an optionally substituted alkenyl, an optionally substituted alkynyl, an optionally substituted cycloalkyl, an optionally substituted heterocyclyl, an optionally substituted aryl, or an optionally substituted heteroaryl; provided that $R^1$ and $R^2$ are not both hydrogen.

Embodiment 2

The compound of embodiment 1, or a pharmaceutically acceptable salt thereof, wherein $R^1$ is an optionally substituted $C_{1-6}$ alkyl.

Embodiment 3

The compound of embodiment 1, or a pharmaceutically acceptable salt thereof, wherein $R^1$ is an unsubstituted $C_{1-6}$ alkyl.

Embodiment 4

The compound of embodiment 1, or a pharmaceutically acceptable salt thereof, wherein $R^1$ is methyl, ethyl, n-propyl, isopropyl, n-butyl, sec-butyl, or tert-butyl.

Embodiment 5

The compound of any one of embodiments 1-4, or a pharmaceutically acceptable salt thereof, wherein $R^2$ is

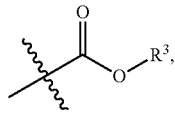

and $R^3$ is an optionally substituted $C_{1-12}$ alkyl, e.g., unsubstituted or substituted with 1, 2, or 3 substituents each independently selected from hydroxyl, carboxyl, halogen (e.g., F), alkyl (e.g., $C_{1-6}$ alkyl), heteroalkyl (e.g., $C_{1-6}$ heteroalkyl), alkoxy (e.g., $C_{1-6}$ alkoyl), aryl (e.g., phenyl), heteroaryl (e.g, 5 or 6 membered heteroaryl), acyl, sulfonyl, sulfhydryl, alkyl sulphanyl, cycloalkyl, heterocyclyl, amino, alkyl amino, dialkyl amino, cyano, ester group, and trifluoromethyl.

Embodiment 6

The compound of embodiment 5, or a pharmaceutically acceptable salt thereof, wherein $R^3$ is a $C_{1-4}$ alkyl (e.g., methyl) optionally substituted with an optionally substituted heterocyclyl group, e.g., $R^2$ is

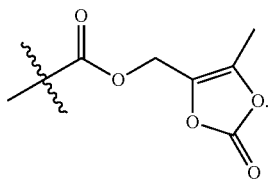 [SMILES: *C(=O)OCc1oc(=O)oc1C]

Embodiment 7

The compound of embodiment 5, or a pharmaceutically acceptable salt thereof, wherein $R^3$ is an unsubstituted linear or branched $C_{1-12}$ alkyl (e.g., n-hexyl).

Embodiment 8

The compound of embodiment 7, or a pharmaceutically acceptable salt thereof, wherein $R^3$ is an unsubstituted linear or branched $C_{1-6}$ alkyl, e.g., ethyl, n-propyl, isopropyl, n-butyl, n-pentyl, or n-hexyl.

Embodiment 9

The compound of embodiment 5, or a pharmaceutically acceptable salt thereof, wherein $R^2$ is

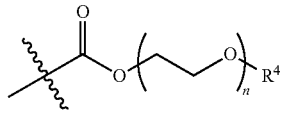

wherein: n is an integer ranging from 1-6; and
$R^4$ is hydrogen, an optionally substituted alkyl (e.g., an optionally substituted aralkyl or heteroaralkyl), an optionally substituted alkenyl, an optionally substituted alkynyl, an optionally substituted cycloalkyl, an optionally substituted heterocyclyl, an optionally substituted aryl, or an optionally substituted heteroaryl.

Embodiment 10

The compound of embodiment 9, or a pharmaceutically acceptable salt thereof, wherein n is 1, 2, or 3.

Embodiment 11

The compound of embodiment 9 or 10, or a pharmaceutically acceptable salt thereof, wherein $R^4$ is hydrogen, a $C_{1-12}$ alkyl (e.g., a $C_{1-6}$ alkyl e.g., ethyl, n-propyl, isopropyl, n-butyl, n-pentyl, or n-hexyl), phenyl, or benzyl.

Embodiment 12

The compound of embodiment 5, or a pharmaceutically acceptable salt thereof, wherein $R^2$ is

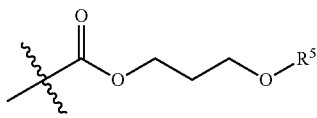

wherein:
$R^5$ is hydrogen, an optionally substituted alkyl (e.g., an optionally substituted aralkyl or heteroaralkyl), an optionally substituted alkenyl, an optionally substituted alkynyl, an optionally substituted cycloalkyl, an optionally substituted heterocyclyl, an optionally substituted aryl, or an optionally substituted heteroaryl.

Embodiment 13

The compound of embodiment 12, or a pharmaceutically acceptable salt thereof, wherein $R^5$ is hydrogen, a $C_{1-12}$ alkyl (e.g., a $C_{1-6}$ alkyl), phenyl, or benzyl.

Embodiment 14

The compound of any one of embodiments 1-4, or a pharmaceutically acceptable salt thereof, wherein $R^2$ is

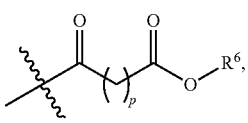

and p is 1, 2, or 3.

Embodiment 15

The compound of embodiment 14, or a pharmaceutically acceptable salt thereof, wherein $R^6$ is hydrogen, or a $C_{1-12}$ alkyl (e.g., a $C_{1-6}$ alkyl).

Embodiment 16

The compound of any one of embodiments 1-4, or a pharmaceutically acceptable salt thereof, wherein $R^2$ is

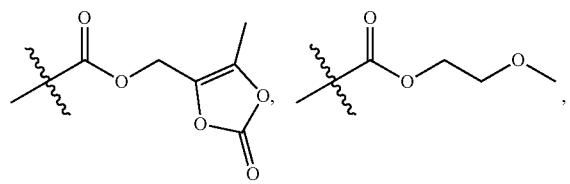

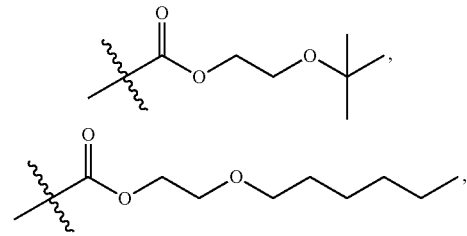

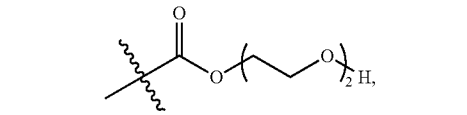

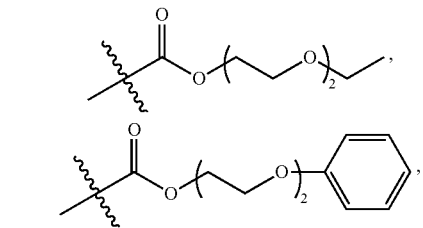

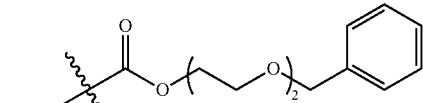

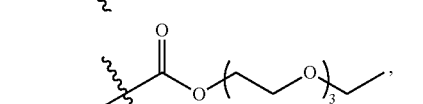

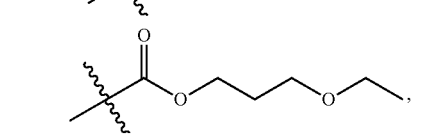

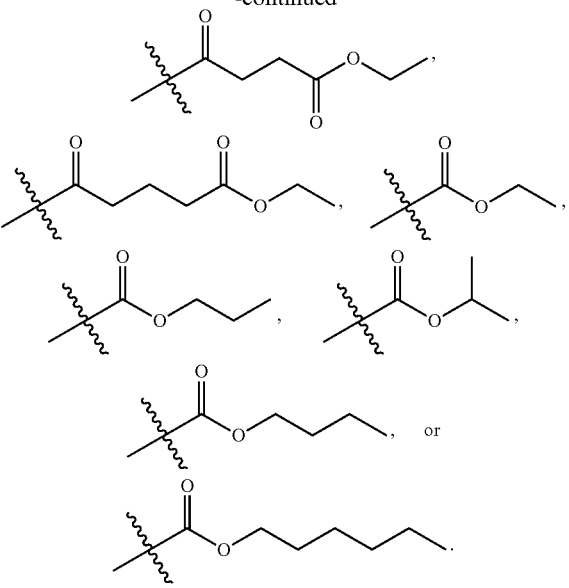

Embodiment 17

The compound of any one of embodiments 1-4, or a pharmaceutically acceptable salt thereof, wherein $R^2$ is

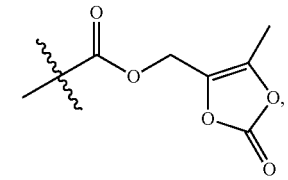

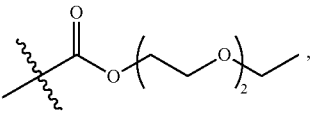

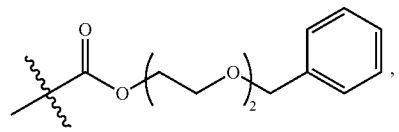

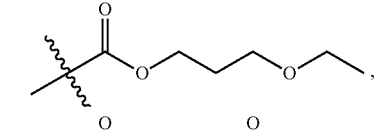

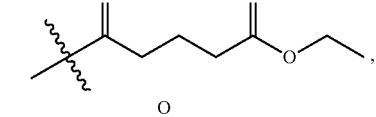

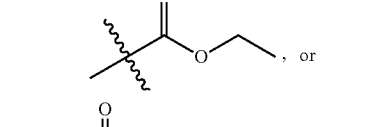

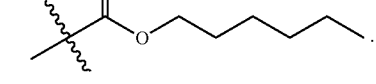

Embodiment 18

A compound selected from Compound Nos. 1-19, or a pharmaceutically acceptable salt thereof.

Embodiment 19

A pharmaceutical composition comprising one or more compounds of any of embodiments 1-18 or a pharmaceutically acceptable salt thereof, and optionally a pharmaceutically acceptable carrier.

Embodiment 20

The pharmaceutical composition of embodiment 19, formulated for oral administration, such as tablet, capsule, pulvis, granule, liquid (e.g., oral solution, suspension, emulsion etc.) or syrup.

Embodiment 21

A method of treating a venous and/or arterial thrombotic disease, comprising administering to a subject in need thereof a therapeutically effective amount of one or more compounds of any of embodiments 1-18 or a pharmaceutically acceptable salt thereof, or the pharmaceutical composition of embodiment 19 or 20.

Embodiment 22

The method of embodiment 21, wherein the thrombotic disease is selected from deep leg vein thrombosis, reocclusion after a bypass operation or angioplasty (PT(C)A), occlusion in peripheral arterial disease, pulmonary embolism, disseminated intravascular coagulation, coronary thrombosis, stroke, and the occlusion of a shunt or stent.

Embodiment 23

A method of reducing the risk of stroke and systemic embolism in a subject with non-valvular atrial fibrillation comprising administering to the subject a therapeutically effective amount of one or more compounds of any of embodiments 1-18 or a pharmaceutically acceptable salt thereof, or the pharmaceutical composition of embodiment 19 or 20.

Embodiment 24

A method of treating deep venous thrombosis and/or pulmonary embolism in a subject in need thereof, comprising administering to the subject a therapeutically effective amount of one or more compounds of any of embodiments 1-18 or a pharmaceutically acceptable salt thereof, or the pharmaceutical composition of embodiment 19 or 20.

Embodiment 25

A method of reducing the risk of recurrence of deep venous thrombosis and/or pulmonary embolism in a subject in need thereof, comprising administering to the subject a therapeutically effective amount of one or more compounds of any of embodiments 1-18 or a pharmaceutically acceptable salt thereof, or the pharmaceutical composition of embodiment 19 or 20.

Embodiment 26

A method of prophylactic treatment of deep venous thrombosis and/or pulmonary embolism in a subject in need thereof, comprising administering to the subject a therapeutically effective amount of one or more compounds of any of embodiments 1-18 or a pharmaceutically acceptable salt thereof, or the pharmaceutical composition of embodiment 19 or 20.

Embodiment 27

The method of embodiment 26, wherein the subject has undergone hip replacement surgery.

Embodiment 28

A method of treating atherosclerosis, coronary artery disease, cerebral arteriopathy, and/or peripheral arteriopathy in a subject in need thereof, comprising administering to the subject a therapeutically effective amount of one or more compounds of any of embodiments 1-18 or a pharmaceutically acceptable salt thereof, or the pharmaceutical composition of embodiment 19 or 20.

Embodiment 29

A method of providing antithrombotic support in thrombolytic treatment, e.g., with rt-PA or streptokinase, in a subject in need thereof, comprising administering to the subject a therapeutically effective amount of one or more compounds of any of embodiments 1-18 or a pharmaceutically acceptable salt thereof, or the pharmaceutical composition of embodiment 19 or 20.

Embodiment 30

A method of preventing long-term restenosis after PT(C)A in a subject in need thereof, comprising administering to the subject a therapeutically effective amount of one or more compounds of any of embodiments 1-18 or a pharmaceutically acceptable salt thereof, or the pharmaceutical composition of embodiment 19 or 20.

Embodiment 31

A method of preventing metastasis, the growth of clot-dependent tumours and/or fibrin-dependent inflammatory processes in a subject in need thereof, comprising administering to the subject a therapeutically effective amount of one or more compounds of any of embodiments 1-18 or a pharmaceutically acceptable salt thereof, or the pharmaceutical composition of embodiment 19 or 20.

Embodiment 32

The method of any one of embodiments 21-31, wherein the administering is via oral administration.

DETAILED DESCRIPTION OF THE INVENTION

One objective of the present invention is to provide a novel orally administrable series of compounds which have significant antithrombotic effects and which have good stability, solubility, pharmacokinetic properties, low toxicity or long-acting effects.

In one embodiment, the present invention provides a novel compound of Formula (I), and its pharmaceutically acceptable salts:

Formula I

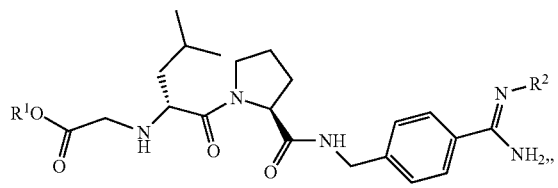

wherein R¹ is hydrogen, an optionally substituted alkyl, an optionally substituted alkenyl, or an optionally substituted alkynyl, and R² is hydrogen,

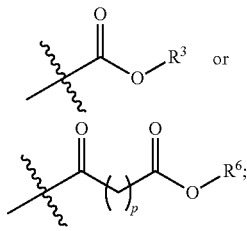

wherein
p is an integer ranging from 1-6, and
R³ is an optionally substituted alkyl (e.g., an optionally substituted aralkyl or optionally substituted heteroaralkyl), an optionally substituted alkenyl, an optionally substituted alkynyl, an optionally substituted cycloalkyl, an optionally substituted heterocyclyl, an optionally substituted aryl, or an optionally substituted heteroaryl; and
R⁶ is hydrogen, an optionally substituted alkyl (e.g., an optionally substituted aralkyl or optionally substituted heteroaralkyl), an optionally substituted alkenyl, an optionally substituted alkynyl, an optionally substituted cycloalkyl, an optionally substituted heterocyclyl, an optionally substituted aryl, or an optionally substituted heteroaryl; provided that R¹ and R² are not both hydrogen.

In some preferred embodiments, R¹ is an optionally substituted $C_{1-6}$ alkyl, for example, R¹ is an unsubstituted $C_{1-6}$ alkyl, preferably, methyl, ethyl, n-propyl, isopropyl, n-butyl, sec-butyl, or tert-butyl.

In some embodiments, R² can be

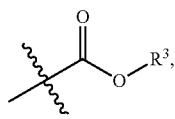

and R³ is an optionally substituted $C_{1-12}$ alkyl, e.g., unsubstituted or substituted with 1, 2, or 3 substituents each independently selected from hydroxyl, carboxyl, halogen (e.g., F), alkyl (e.g., $C_{1-6}$ alkyl), heteroalkyl (e.g., $C_{1-6}$ heteroalkyl), alkoxy (e.g., $C_{1-6}$ alkoyl), aryl (e.g., phenyl), heteroaryl (e.g, 5 or 6 membered heteroaryl), acyl, sulfonyl, sulfhydryl, alkyl sulphanyl, cycloalkyl, heterocyclyl, amino, alkyl amino, dialkyl amino, cyano, ester group, and trifluoromethyl.

In some embodiments, R³ can be a $C_{1-4}$ alkyl optionally substituted with an optionally substituted heterocyclyl group. For example, in some preferred embodiments, R² can be

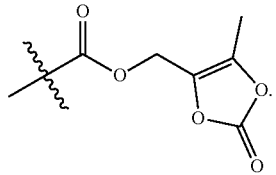 [SMILES: *C(=O)OCc1oc(=O)oc1C]

In some embodiments, R³ can be an unsubstituted linear or branched $C_{1-12}$ alkyl (e.g., n-hexyl). For example, in some embodiments, R³ can be an unsubstituted linear or branched $C_{1-6}$ alkyl, e.g., ethyl, n-propyl, isopropyl, n-butyl, n-pentyl, or n-hexyl.

In some embodiments, R² is

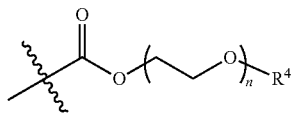

wherein: n is an integer ranging from 1-6; and
R⁴ is hydrogen, an optionally substituted alkyl (e.g., an optionally substituted aralkyl or heteroaralkyl), an optionally substituted alkenyl, an optionally substituted alkynyl, an optionally substituted cycloalkyl, an optionally substituted heterocyclyl, an optionally substituted aryl, or an optionally substituted heteroaryl. In some embodiments, n can be 1, 2, or 3. In some embodiments, R⁴ can be hydrogen, a $C_{1-12}$ alkyl (e.g., a $C_{1-6}$ alkyl e.g., ethyl, n-propyl, isopropyl, n-butyl, n-pentyl, or n-hexyl), phenyl, or benzyl.

In some embodiments, R² can be

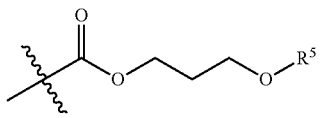

wherein:
R⁵ is hydrogen, an optionally substituted alkyl (e.g., an optionally substituted aralkyl or heteroaralkyl), an optionally substituted alkenyl, an optionally substituted alkynyl, an optionally substituted cycloalkyl, an optionally substituted heterocyclyl, an optionally substituted aryl, or an optionally substituted heteroaryl. In some embodiments, R⁵ can be hydrogen, a $C_{1-12}$ alkyl (e.g., a $C_{1-6}$ alkyl as described herein), phenyl, or benzyl.

In some embodiments, R² can be

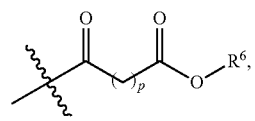

wherein p is 1, 2, or 3. In some embodiments, R⁶ can be hydrogen, or a $C_{1-12}$ alkyl (e.g., a $C_{1-6}$ alkyl).

In some preferred embodiments, when the "optionally substituted" group for $R^1$ or $R^2$ in Formula (I) contains a substituent, such as 1, 2 or 3 substituents, the "substituent" can be preferably independently selected from $C_{1-4}$ alkyl (e.g., methyl, ethyl etc.), halogen (especially fluorine), or trifluoromethyl.

In some preferred embodiments, $R^2$ can be

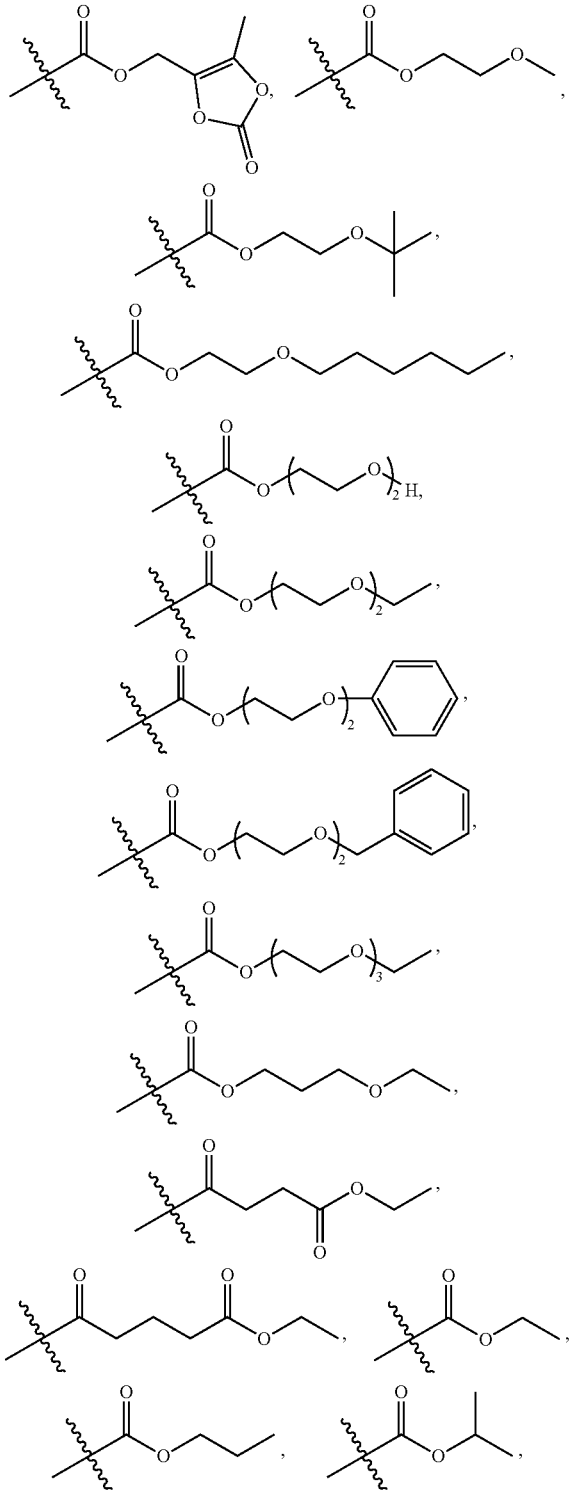

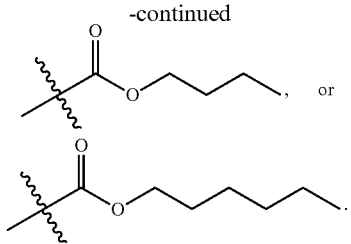

In some preferred embodiments, $R^2$ can be

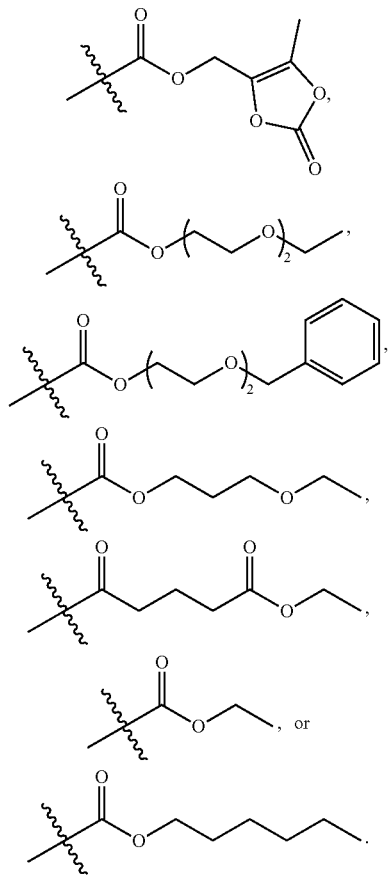

In some embodiments, $R^1$ in Formula (I) can be hydrogen.
In some embodiments, $R^2$ in Formula (I) can be hydrogen.

Definitions

In accordance to common practice in the art, the symbol, ∼∼∼, appearing in chemical structures herein, indicates the point at which the displayed moiety is attached to the remainder of the molecule.

The term "alkyl" as used herein, refers to a straight or branched saturated hydrocarbon chain, such as a straight or branched saturated hydrocarbon chain containing from 1 to 20 carbon atoms. The term "Cx-y alkyl" refers to a straight or branched saturated hydrocarbon containing from x to y carbon atoms. For example, "$C_{1-6}$ alkyl" means a straight or branched saturated hydrocarbon having 1 to 6 carbon atoms. Representative examples of alkyl groups include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-decyl and n-decyl.

The term "alkenyl" as used herein, refers to a straight or branched hydrocarbon chain containing at least one carbon-carbon double bond, such as a straight or branched hydrocarbon chain containing from 2 to 20 carbons and containing at least one carbon-carbon double bond. The term "Cx-y alkenyl" refers to a straight or branched hydrocarbon chain containing from x to y carbon atoms containing at least one carbon-carbon double bond. For example, the term "$C_{3-6}$ alkenyl" refers to an alkenyl group containing from 3 to 6 carbon atoms. Representative examples of alkenyl include, but are not limited to, butane-2,3-dienyl, vinyl, 2-propenyl, 2-methyl-2-propenyl, 3-butenyl, 4-pentenyl, 5-hexenyl, 2-heptenyl, 2-methyl-1-heptenyl and 3-decenyl.

The term "alkynyl" as used herein, refers to a straight or branched alkyne group containing at least one carbon-carbon triple bond, such as a straight or branched chain containing from 2 to 20 carbon atoms and containing at least one carbon-carbon triple bond. The term "Cx-y alkynyl" refers to a straight or branched hydrocarbon group containing from x to y carbon atoms. For example: "$C_{3-6}$ alkynyl" refers to a straight or branched chain hydrocarbon radical containing from 3 to 6 carbon atoms and containing at least one carbon-carbon triple bond. Representative examples of alkynyl include, but are not limited to, ethynyl, 1-propynyl, 2-propynyl, 3-butynyl, 2-pentynyl, and 1-butynyl.

The term "heteroalkyl" as used herein, refers to a group in which one or more $CH_2$ or CH in an alkyl group is replaced by independently selected O, S, S(O), $SO_2$, N or NH.

The term "aralkyl" as used herein, refers to an alkyl group substituted with one or more independently selected aryl groups.

The term "heteroaralkyl" as used herein, refers to an alkyl group substituted with one or more independently selected heteroaryl groups.

The term "alkoxy" as used herein refers to "O—$R^a$", wherein $R^a$ is alkyl.

The term "cycloalkoxy" as used herein refers to "O—$R^a$" wherein $R^a$ is cycloalkyl or heterocycloalkyl.

The term "cycloalkyl" as used herein refers to a monocyclic or bridged carbocyclic ring system. Monocyclic cycloalkyl groups are carbocyclic systems containing from 3 to 10 carbon atoms, zero heteroatoms, saturated or unsaturated (non-aromatic rings). Examples of saturated monocyclic systems include cyclopropyl, cyclobutyl, cyclopentyl, cyclohexyl, cycloheptyl and cyclooctyl. A saturated monocyclic ring may contain one or two alkylene bridges, each comprising one, two or three carbon atoms, each bridge connecting two non-adjacent carbon atoms of the ring system. Representative examples of such bridged cycloalkyl ring systems include, but are not limited to, bicyclo[3.1.1] heptane, bicyclo [2.2.1] heptane, bicyclo [2.2.2] octane, Bicyclo[3.2.2]decane, bicyclo[3.3.1]decane, bicyclo[4.2.1] nonane, tricyclo[3.3.1.0 3,7]decane (octahydro-2,5-methylenecyclopentadiene or noradamantane) and tricyclo[3.3.1.1 3,7]decane (adamantane). Some unsaturated monocyclic rings may contain an olefinic bond having four to ten carbon atoms and zero heteroatoms. For example, a four-membered ring system can have one double bond, a five- or six-membered ring system can have one or two double bonds, a seven- or eight-membered ring system can have one, two or three double bonds, and a nine- or ten-membered ring can have one or two, three or four double bonds. Representative examples of unsaturated monocyclic cycloalkyl include, but are not limited to, cyclobutenyl, cyclopentenyl, cyclohexenyl, cycloheptenyl, and cyclooctenyl. The unsaturated monocyclic ring may also contain one or two alkylene bridges, each comprising one, two or three carbon atoms, each bridging two non-adjacent carbon atoms of the ring system. Representative examples of unsaturated bridged rings containing olefinic bonds include, but are not limited to, 4,5,6,7-tetrahydro-3aH-indane, octahydronaphthyl, and 1,6-dihydro-cyclopentadiene. Monocyclic and bridged cycloalkyl groups can be attached to the parent molecular moiety through any substitutable atom contained within the ring system The term "heterocycle" or "heterocycloalkyl" or "heterocycloalkylene" as used herein, refers to a monocyclic or bridged three, four, five, six, seven or eight membered ring system containing at least one heteroatom, saturated or unsaturated (non-aromatic), the heteroatoms being independently selected from the group consisting of O, N and S. The nitrogen and sulfur heteroatoms in the heterocycle can be optionally oxidized, and the nitrogen atom can optionally be quaternized. Representative examples of saturated heterocycloalkyl groups include, but are not limited to, morpholinyl, tetrahydropyranyl, pyrrolidinyl, piperidinyl, dioxolanyl, tetrahydrofuranyl, thiomorpholinyl, 1,4-dioxanyl, tetrahydrothiophenyl, tetrahydrothiopyranyl, oxetane, piperazinyl, imidazolidinyl, azetidine, azepanyl, aziridinyl, diazepanyl, dithiatyl, dithianyl, isoxazolidinyl, isothiazolidinyl, oxadiazolidinyl, oxazolidinyl, pyrazolidinyl, tetrahydrothiophenyl, thiadiazolidinyl, thiazolidinyl, thiomorpholinyl, trithiaalkyl and trithiaalkyl. Representative examples of unsaturated heterocycles such as heterocycles containing olefinic bonds include, but are not limited to, 1,4,5,6-tetrahydropyridazinyl, 1,2,3,6-tetrahydropyridyl, dihydropyranyl, imidazolinyl, isothiazolinyl, oxadiazolyl, isoxazolinyl, oxazolinyl, pyranyl, pyrazolinyl, pyrrolinyl, thiadiazolyl, thiazolyl and thiopyranyl. Unsaturated heterocycles also include the following:

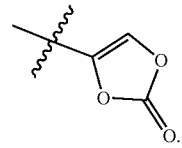

The monocyclic and bridged heterocycles can be attached to the parent molecular moiety through any substitutable carbon atom or any substitutable nitrogen atom contained within the ring.

The term "aryl" as used herein, refers to a monocyclic or polycyclic aromatic ring that does not contain a heteroatom, such as phenyl or naphthyl.

The term "heteroaryl ring" or "heteroaryl" or "heteroarylene" as used herein, refers to 5 or 6 membered aromatic ring having at least one carbon atom and one or more independently selected nitrogen, oxygen or sulfur atom. The heteroaryl ring of the present invention can be attached through any adjacent atom in the ring, provided that the normal valence is maintained. Representative examples of heteroaryl include, but are not limited to, furanyl (including but not limited to: furan-2-yl), imidazolyl (including but not limited to: IH-imidazol-1-yl), isoxazolyl, isothiazolyl, oxadiazolyl, 1,3-oxazolyl, pyridyl (e.g., pyridin-4-yl, pyridin-2-yl and pyridin-3-yl), pyridazinyl, pyrimidinyl, pyrazinyl, pyrazolyl, pyrrolyl, tetrazolyl, thiadiazolyl, 1,3-thiazolyl, thienyl (including but not limited to: thiophen-2-yl and thiophen-3-yl), triazolyl and triazinyl. For example, heteroaryl include the structural unit represented by formula (II):

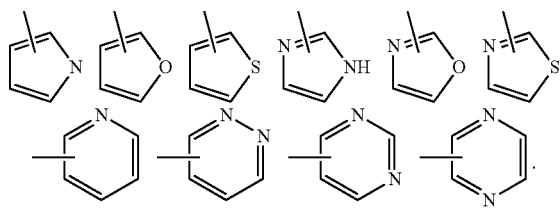

The term "optionally substituted" as used herein means that the group being modified can be unsubstituted or substituted, for example, substituted with 1, 2 or 3 substituents. When the "optionally substituted" group contains a substituent, such as 1, 2 or 3 substituents, the "substituent" can be independently selected from the group consisting of hydroxyl, carboxyl, halogen, alkyl, alkoxy, aryl, heteroaryl, acyl, sulfonyl, —SH, alkylthio, cycloalkyl, heterocycloalkyl, amino, alkylamino, dialkylamino, cyano, ester or trifluoromethyl, each of the foregoing (e.g., alkyl, etc.) can be further optionally substituted with, for example, 1, 2 or 3 independently selected substituents. In some cases, when the "optionally substituted" group contains a substituent, such as 1, 2 or 3 substituents, the "substituent" can be preferably independently selected from $C_{1-4}$ alkyl (e.g., methyl, ethyl etc.), halogen (especially fluorine), or trifluoromethyl. For example, "optionally substituted alkyl" includes unsubstituted alkyl, and also includes alkyl substituted with 1, 2 or 3 substituents independently selected from hydroxy, carboxy, halo (e.g., F), alkyl (e.g., $C_{1-6}$ alkyl), heteroalkyl (e.g., $C_{1-6}$ heteroalkyl), alkoxy (e.g., $C_{1-6}$ alkoxy), aryl (e.g., phenyl), heteroaryl (e.g., 5 or 6 membered heteroaryl), acyl, sulfonyl, —SH, alkylthio, cycloalkyl, heterocycloalkyl, amino, alkylamino, dialkylamino, cyano, ester and trifluoromethyl.

"Compound(s) of the present invention" includes any compound of formula (I) (such as any one or more of compounds 1-19), pharmaceutically acceptable salts, stereoisomers thereof, tautomers thereof, isotopes, etc. Compounds of the present invention may also exist in the form of hydrates or solvates. Exemplary embodiments of compounds of the present invention include those described in Embodiments 1-18. Those skilled in the art would understand that Compounds of the present invention may also exist in a tautomeric mixture.

Compounds of the present invention contain an asymmetric carbon atom in R or S configuration. Preferably, the two chiral centers of formula (I) of the present invention are present predominantly in the configuration shown, for example, greater than 80% ee for each chiral center. For example, in some embodiments, in compounds of the present invention, for each chiral center, the configuration shown in Formula (I) is about 85% to 90% more than the other configuration, more preferably about 95% to 99%, more preferably about 99%, or the other configuration cannot be detected.

Compounds of the present invention may exist in isotopically labeled or enriched forms comprising one or more atoms having an atomic mass or mass number different from the atomic mass or mass number of the largest amount found in nature. An isotope can be a radioactive or non-radioactive isotope. Isotopes of atoms such as hydrogen, carbon, phosphorus, sulfur, fluorine, chlorine and iodine include, but are not limited to: $^{2}H$, $^{3}H$, $^{13}C$, $^{14}C$, $^{15}N$, $^{18}O$, $^{32}P$, $^{35}S$, $^{18}F$, $^{36}Cl$ and $^{125}I$. Compounds containing these isotopes and/or isotopes of other atoms are within the scope of the invention.

Certain preferred specific compounds of the present invention include but are not limited to the following:

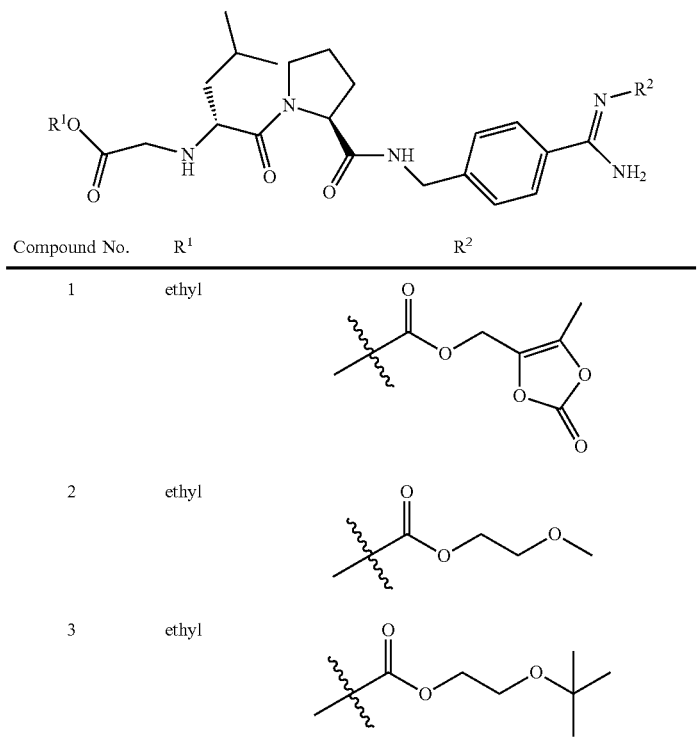

-continued

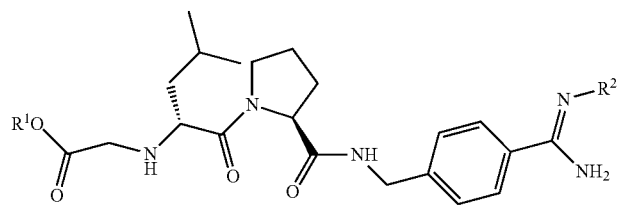

| Compound No. | R¹ | R² |
|---|---|---|
| 4 | ethyl | −C(CH₃)₂−C(O)O−CH₂CH₂−O−(CH₂)₅CH₃ |
| 5 | ethyl | −C(CH₃)₂−C(O)O−(CH₂CH₂O)₂H |
| 6 | ethyl | −C(CH₃)₂−C(O)O−(CH₂CH₂O)₂−CH₂CH₃ |
| 7 | ethyl | −C(CH₃)₂−C(O)O−(CH₂CH₂O)₂−C₆H₅ |
| 8 | ethyl | −C(CH₃)₂−C(O)O−(CH₂CH₂O)₂−CH₂C₆H₅ |
| 9 | ethyl | −C(CH₃)₂−C(O)O−(CH₂CH₂O)₃−CH₂CH₃ |
| 10 | ethyl | −C(CH₃)₂−C(O)O−CH₂CH₂CH₂−O−CH₂CH₃ |
| 11 | ethyl | −C(CH₃)₂−C(O)−CH₂CH₂−C(O)O−CH₂CH₃ |
| 12 | ethyl | −C(CH₃)₂−C(O)−CH₂CH₂CH₂−C(O)O−CH₂CH₃ |
| 13 | ethyl | −C(CH₃)₂−C(O)O−CH₂CH₃ |

-continued

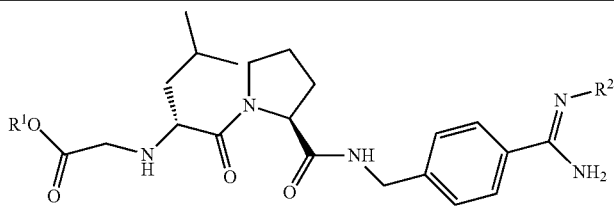

| Compound No. | R¹ | R² |
|---|---|---|
| 14 | ethyl | propyl ester group |
| 15 | ethyl | isopropyl ester group |
| 16 | ethyl | butyl ester group |
| 17 | ethyl | hexyl ester group |
| 18 | n-propyl | hexyl ester group |
| 19 | tert-butyl | hexyl ester group |

More preferred specific compounds are the following:

| Compound No. | R¹ | R² |
|---|---|---|
| 1 | ethyl | (5-methyl-2-oxo-1,3-dioxol-4-yl)methyl ester group |

-continued

| Compound No. | R¹ | R² |
|---|---|---|
| 6 | ethyl | 2-(2-ethoxyethoxy)ethyl ester group |

-continued

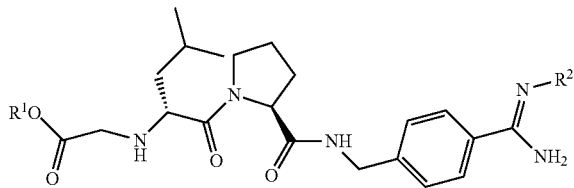

| Compound No. | R¹ | R² |
|---|---|---|
| 8 | ethyl | ![structure] |
| 10 | ethyl | ![structure] |
| 12 | ethyl | ![structure] |
| 13 | ethyl | ![structure] |
| 17 | ethyl | ![structure] |
| 19 | tert-butyl | ![structure] |

The present disclosure also includes pharmaceutically acceptable salts of the compounds herein.

The compounds of formula (I) of the present invention are useful for mediating the activity of tryptase-like serine proteases. More specifically, compounds of the present invention are useful as anticoagulants and agents for modulating or inhibiting the activity of tryptase-like serine proteases, thereby treating thromboembolic diseases and other related cardiovascular diseases.

Unless otherwise stated, the terms and abbreviations disclosed in the present invention have their ordinary meanings as understood by those skilled in the art.

Pharmaceutically acceptable salts of the compounds of formula (I) include pharmaceutically acceptable inorganic and organic acid addition salts. Examples of suitable acids include, but are not limited to, sulfuric acid, sulfurous acid, hydrochloric acid, hydrobromic acid, nitric acid, phosphoric acid, metaphosphoric acid, pyrophosphoric acid, maleic acid, fumaric acid, succinic acid, citric acid, malic acid, perchloric acid, Tartaric acid, formic acid, acetic acid, propionic acid, heptanoic acid, oxalic acid, benzoic acid, salicylic acid, cinnamic acid, methanesulfonic acid, benzenesulfonic acid, p-toluenesulfonic acid, lactic acid, nicotinic acid, and mandelic acid.

A second object of the present invention is to provide a process for the preparation of a compound of formula (I), which comprises preparing a final product starting from an N-protected amino acid. The process can be carried out with similar conventional reactions known in the art (compounds of the invention can be prepared according to the following general procedures). Starting materials, reagents, techniques and methods used in the synthetic routes are also known and understood by those skilled in the art.

Compounds of the present invention can be prepared according to the following general procedure:

Route 1:

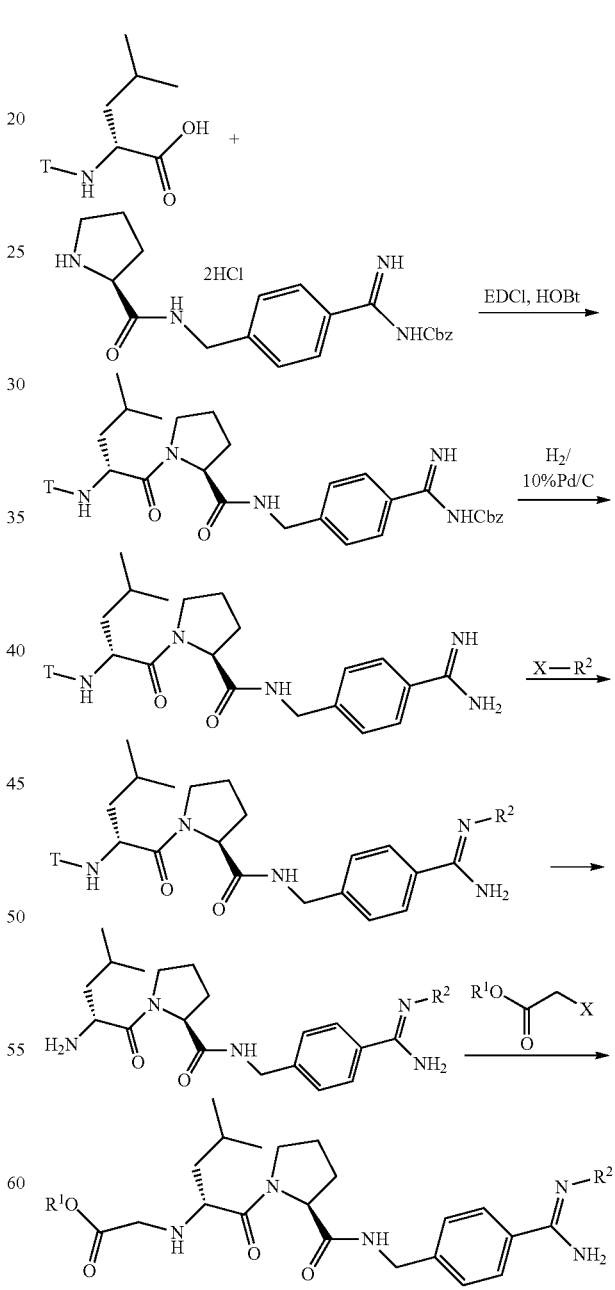

A protected amino acid such as N-tert-butoxycarbonyl-D-leucine can be coupled with a desired amine using a coupling agent such as EDCI/HOBt. The product can then be converted into an amidine through hydrogenation. A R² group can then be attached to the amidine. After removing the protecting group T, the deprotected product can then be converted into the final compound with a nucleophilic substitution reaction.

Route 2:

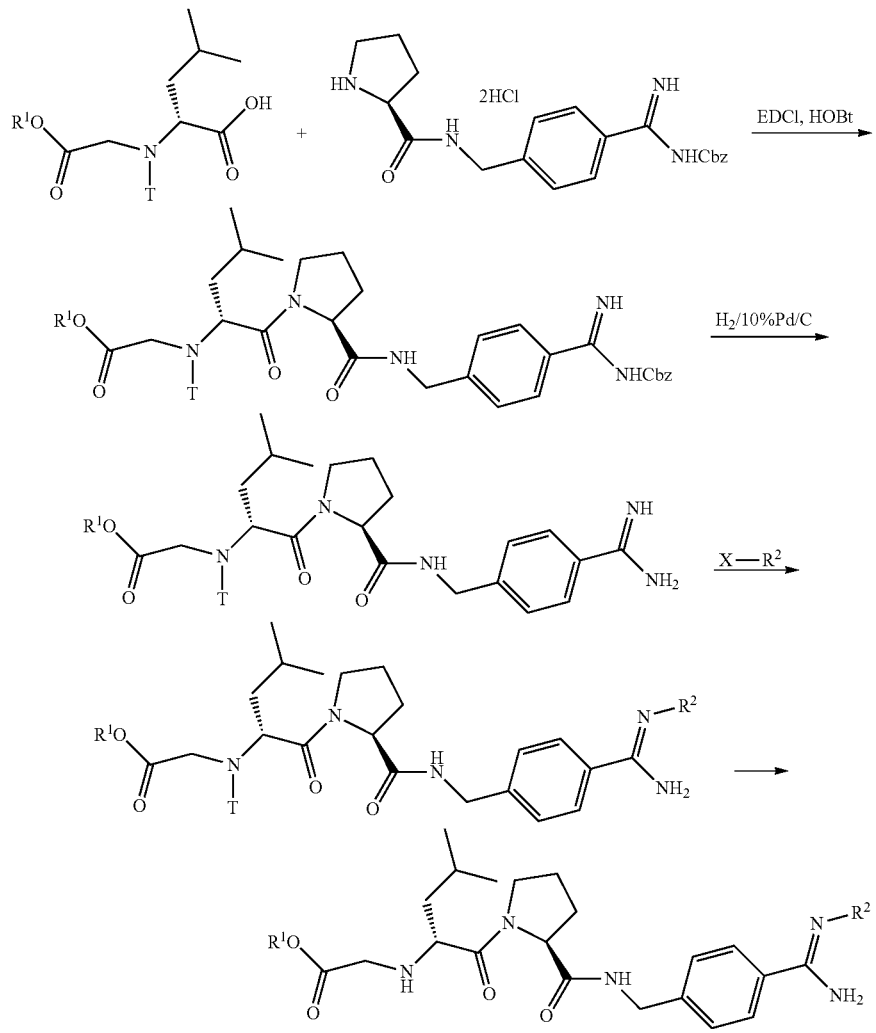

Protected amino acid, to which the modifying group has been attached, can be coupled with a desired amine using a coupling agent such as EDCI/HOBt. The coupling product can then be converted into an amidine after removing the protecting group by hydrogenation. A R² group can then be attached to the amidine. After removing the protecting group T, the deprotected product can then be converted into the final compound with a nucleophilic substitution reaction.

In the above synthetic routes, the amide coupling reaction can use a standard peptide coupling method, for example, those mediated by an azide, a mixed acid anhydride, a carbodiimide (dicyclohexylcarbodiimide DCC, diisopropylcarbodiimide EDC), an active ester, a carbonyl diimidazole, a phosphorus reagent such as a BOP-Cl. Some of these methods (especially the carbodiimide method) can be facilitated by addition of 1-hydroxybenzotriazole. The process can be carried out under an inert gas such as nitrogen, and if necessary, the coupling reaction can be carried out in the presence of an acid scavenger. Examples of suitable acid scavengers include organic tertiary amines such as diisopropylethylamine, triethylamine, trimethylamine, pyridine, N-methylmorpholine or the like, preferably N-methylmorpholine or diisopropylethylamine.

The above coupling reaction is usually carried out in an anhydrous solvent. Examples of useful solvents include, but are not limited to, dichloromethane, tetrahydrofuran, diethyl ether, acetonitrile, dichloroethane, ethyl acetate, N,N-dimethylformamide, and dimethyl sulfoxide. The reaction temperature is usually not critical, preferably the reaction is carried out at 0 to 30° C. for 2 to 24 hours.

N-deprotection can be carried out by a conventional method such as acid mediated hydrolysis, such as using an organic acid such as trifluoroacetic acid, benzenesulfonic acid, formic acid or the like, or a mineral acid such as hydrochloric acid, sulfuric acid, hydrobromic acid or the like; a base-mediated hydrolysis, such as using an alkali metal or alkaline earth metal hydroxide, hydride, carbonate or hydrogencarbonate such as sodium hydroxide, potassium hydroxide, sodium hydride, potassium carbonate, sodium hydrogencarbonate, etc., or an organic base such as diisopropylethylamine, triethylamine, piperidine, etc.; or hydrogenolysis in the presence of a catalyst such as a metal catalyst such as palladium, platinum, or nickel. Suitable methods can also be found in "Protective Groups in Organic Synthesis" Third Edition, T. W. Green and Peter G. M. Wuts (1999), Publisher: John Wiley & Sons, Inc.

In general, removing the amino protecting group can be carried out in a solvent that does not adversely influence the reaction. Examples of useful solvents include: dichloromethane, alcohol (e.g., methanol, ethanol, etc.), tetrahydrofuran, dioxane, acetone, acetic acid, and ethyl acetate. The reaction temperature is usually not critical, preferably 0 to 40° C.

N-alkylation can be carried out with a nucleophilic substitution. Suitable nucleophilic substitution reagents include, but are not limited to, alkyl bromides, alkyl iodides, alkyl chlorides, alkyl sulfonates, alkyl benzene sulfonates, alkyl p-toluene sulfonates, alkyl mesylate or a reagent containing a sulfate group such as dimethyl sulfate. Alkyl iodide or alkyl p-toluenesulfonate is preferred. Nucleophilic substitution reactions are generally carried out in the presence of an acid scavenger, and appropriate acid scavengers can be an inorganic base, such as alkali or alkaline earth metal hydroxides, hydrides, carbonates, hydrogencarbonates, hydrogen phosphates such as sodium hydroxide, sodium hydride, potassium carbonate, dipotassium hydrogen phosphate, etc., or organic bases such as diisopropylethylamine, triethylamine, trimethylamine, pyridine, N-methylmorpholine or the like, preferably dibasic potassium hydrogen phosphate or diisopropylethylamine. Examples of useful solvents include, but are not limited to, tetrahydrofuran, dioxane, acetonitrile, acetone, N,N-dimethylformamide, and the like. The reaction temperature can be adjusted, preferably 20 to 80° C.

The product of each step can be purified by methods known in the art such as column chromatography and recrystallization.

A third object of the present invention is to provide a use of compounds of the formula (I) for inhibiting thrombin and for the use in the prevention and/or treatment of thrombin-mediated and/or thrombin-related diseases. As described in the Examples section herein, representative compounds of formula (I) were shown to have significant antithrombotic effects in animal models. The methods of using Compounds of the present invention typically include administering a compound of the present invention, such as a compound of formula (I), such as any one or more of compounds 1-19, or a pharmaceutically acceptable salt, to a subject in need thereof (e.g., in need of prevention or treatment of any of the thrombin-mediated or thrombin-related disease described herein) in an effective amount, such as in a therapeutically effective amount. Exemplary methods of using Compounds of the present invention include any of those described in Embodiments 21-32.

In some embodiments, the Compounds of the present invention can be used in replacement of dabigatran etexilate for any of the indications that dabigatran etexilate is indicated as useful. Non-limiting indications that dabigatran etexilate is indicated as useful include any of the US FDA approved indications for dabigatran etexilate mesylate (Pradaxa), indications approved by similar agencies outside of the U.S., and any of such indications that dabigatran etexilate is indicated as useful as described in U.S. Pat. Nos. 6,087,380, 7,866,474, 7,932,273, 9,034,822, and 9,925,174, the content of each of which is incorporated by reference in its entirety.

Compounds of the present invention are useful in the prevention and/or treatment of thrombin-mediated and thrombin-related diseases. In some embodiments, the present invention provides a use of a compound of the present invention, such as a compound of formula (I), such as any one or more of compounds 1-19, or a pharmaceutically acceptable salt, for the prevention and/or treatment of thrombotic diseases, especially venous or arterial thromboembolism, such as deep vein thrombosis in the lower limb, reocclusion after bypass surgery or angioplasty, obstruction of peripheral arterial disease, coronary thromboembolism, etc. In some embodiments, the present invention provides a method of treating or preventing a thrombotic disease, such as venous or arterial thromboembolism, such as deep vein thrombosis in the lower limb, reocclusion after bypass surgery or angioplasty, obstruction of peripheral arterial disease, coronary thromboembolism, the method comprising administering a compound of the present invention, such as a compound of formula (I), such as any one or more of compounds 1-19, or a pharmaceutically acceptable salt, to a subject in need thereof in an effective amount, such as in a therapeutically effective amount.

In some embodiments, the present invention provides a use of a compound of the present invention, such as a compound of formula (I), such as any one or more of compounds 1-19, or a pharmaceutically acceptable salt, for the prevention and/or treatment of thrombosis related diseases or disorders such as stroke, pulmonary embolism, myocardial or cerebral infarction, atrial fibrillation and arrhythmia. In some embodiments, the present invention provides a method of treating or preventing a thrombosis related disease or disorder, such as one or more diseases or disorders selected from stroke, pulmonary embolism, myocardial or cerebral infarction, atrial fibrillation and arrhythmia, the method comprising administering a compound of the present invention, such as a compound of formula (I), such as any one or more of compounds 1-19, or a pharmaceutically acceptable salt, to a subject in need thereof in an effective amount, such as in a therapeutically effective amount.

In some embodiments, the present invention provides a use of a compound of the present invention, such as a compound of formula (I), such as any one or more of compounds 1-19, or a pharmaceutically acceptable salt, for the prevention and/or treatment of atherosclerotic diseases such as Coronary artery disease, cerebral arterial disease, and peripheral arterial disease. In some embodiments, the present invention provides a method of treating or preventing an atherosclerotic disease or disorder, such as one or more diseases or disorders selected from Coronary artery disease, cerebral arterial disease, and peripheral arterial disease, the method comprising administering a compound of the present invention, such as a compound of formula (I), such as any one or more of compounds 1-19, or a pharmaceutically acceptable salt, to a subject in need thereof in an effective amount, such as in a therapeutically effective amount.

In some embodiments, the present invention provides a use of a compound of the present invention, such as a compound of formula (I), such as any one or more of compounds 1-19, or a pharmaceutically acceptable salt, for the prevention and/or treatment of any oncological disease. In some embodiments, the present invention provides a method of treating or preventing an oncological disease or disorder, the method comprising administering a compound of the present invention, such as a compound of formula (I), such as any one or more of compounds 1-19, or a pharmaceutically acceptable salt, to a subject in need thereof in an effective amount, such as in a therapeutically effective amount.

Compounds of the present invention can also act as anticoagulants in in vitro or ex vivo blood lines. In some embodiments, the present invention provides a method of inhibit coagulation in in vitro or ex vivo blood lines, the method comprising adding a compound of the present invention, such as a compound of formula (I), such as any one or more of compounds 1-19, or a pharmaceutically acceptable salt, to in vitro or ex vivo blood line in an effective amount.

Additionally, the compounds described herein (such as any one or more of compounds 1-19 or a pharmaceutically acceptable salt) can be used in combination with a thrombolytic agent, for example, to reduce reperfusion time and prolong reocclusion time. In some embodiments, the present invention provides a method of reduce reperfusion time and/or prolong reocclusion time, the method comprising administering a compound of the present invention, such as a compound of formula (I), such as any one or more of compounds 1-19, or a pharmaceutically acceptable salt, to a subject in need thereof in an effective amount, wherein the subject is also administered a thrombolytic agent. Furthermore, compounds of the present invention can be used to prevent the re-formation of thrombi after microsurgery. In some embodiments, the present invention provides a method of preventing re-formation of thrombi after microsurgery, the method comprising administering a compound of the present invention, such as a compound of formula (I), such as any one or more of compounds 1-19, or a pharmaceutically acceptable salt, to a subject in need thereof in an effective amount. Compounds of the present invention are also effective for use in hemodialysis and anticoagulant therapy for disseminated intravascular coagulation. In some embodiments, the present invention provides a method of providing a hemodialysis and anticoagulant therapy for disseminated intravascular coagulation, the method comprising administering a compound of the present invention, such as a compound of formula (I), such as any one or more of compounds 1-19, or a pharmaceutically acceptable salt, to a subject in need thereof in an effective amount. Compounds of the present invention are also useful for the in vitro preservation of blood, plasma and other blood products. In some embodiments, the present invention provides a method of preserving blood, plasma, or other blood products, the method comprising adding a compound of the present invention, such as a compound of formula (I), such as any one or more of compounds 1-19, or a pharmaceutically acceptable salt, to the blood, plasma or other blood product, e.g., in an effective amount to prevent coagulation of the blood, plasma or other blood product.

Compounds of the present invention can be administered orally. The amount will depend on the particular circumstances of the treated subject, including the route of administration, the frequency of administration, the condition being treated, and the like. A typical oral daily dose can be between about 0.01 mg/kg and about 1000 mg/kg. It can be a single daily dose, or multiple doses per day such as 2 to 4 times a day. The dosage and mode of administration can be adjusted depending on the age and weight of the patient as well as the severity of the condition treated. Typically, the subject herein is an animal, preferably a mammal, most preferably a human.

A fourth object of the present invention is to provide a pharmaceutical composition, which comprises a compound of the present invention, such as a compound of formula (I) (such as any one or more of compounds 1-19) or pharmaceutically acceptable salts, and optionally one or more pharmaceutically acceptable excipients.

Compounds of the present invention can be administered in the form of a pharmaceutical composition. For example, for oral administration, compounds of the present invention can be in the form of a tablet, a capsule, a powder, a granule, a liquid preparation (for example, an oral solution, a suspension, an emulsion, etc.) or a syrup, which can contain a pharmaceutically acceptable excipient such as a lubricant, a binder, a disintegrant, a filler, a dispersing agent, an emulsifier, a stabilizer, and the like.

For example, for an injectable formulation, the compound(s) of the present invention can be mixed or dissolved in physiological saline, and a suitable dilute acid or base or buffer salt can be added to adjust the pH, which can also include an antioxidant or a metal chelating agent. The solution can be sterilized by filtration and filled under sterile conditions in a sterile ampoules.

For example, tablets can be prepared by thoroughly mixing the compound(s) of the present invention with excipients (such as microcrystalline cellulose, sodium carboxymethyl starch, corn starch, magnesium stearate, talc, etc.) to provide a mixture, which can then be sieved, and compressed using a tablet machine. For example, a hard capsule can be prepared by sieving the compound(s) of the present invention with an excipient (e.g., dry starch, magnesium stearate, etc.) and then filling the mixture into a hard gelatin capsule using suitable equipment.

For the preparation of suspensions, the compound(s) of the present invention can be sieved and mixed with excipients such as sodium carboxymethylcellulose and syrup to form a uniform paste. In some cases, pigment, benzoic acid, etc. can be diluted with a portion of purified water, which can then be added to the paste with agitation. Water is then added to produce a desired volume. Other methods of preparing pharmaceutical compositions, excipients and the like can be found in Remington's Pharmaceutical Sciences, 18th Ed., Alfonso R. Gennaro (1990), publisher: Mack Publishing Company and its updates.

The pharmaceutical composition of the present invention can be a solid, semi-solid or liquid preparation made by conventional techniques. These methods include, for example, mixing, dissolving, granulating, grinding, emulsifying, embedding, spray drying or freeze drying. The active ingredient in such compositions can comprise from 0.1% to 99.9% by weight of the formulation. The carrier, diluent or excipient used in the compositions are compatible with the active ingredient and are pharmaceutically acceptable.

The following abbreviations may be used in this application:

Boc: t-butyloxycarbonyl
Cbz: benzyloxycarbonyl
Leu: leucine
Pro: prolyl
DIEA: diisopropylethylamine
EDCI: 1-ethyl-3-(3-dimethylaminopropyl) carbodiimide hydrochloride
HOBt: 1-hydroxybenzotriazole
MSA: methanesulfonic acid
AcOH: acetic acid
DMF: N,N-dimethyl formamide Biological Activity Compounds of the present invention typically have improved properties, characterized by excellent solubility, rapid activation, good oral bioavailability, significant biological activity, and low toxicity.

One advantage of compounds of the present invention is that they can be absorbed in the gastrointestinal tract. Compounds of the present invention have higher lipophilicity relative to the compound of formula (V), which enhances passive diffusion of the compounds of the present invention across the lipid bilayer cell membrane. Therefore, compounds of the present invention can have significantly improved oral bioavailability. Further, compounds of the present invention can be rapidly absorbed and metabolized into the active compound of formula (V). In vitro and in vivo studies show that representative compounds formula (I) can be hydrolyzed into a compound of formula (III) and/or formula (IV) with an esterase and ultimately converted into a compound of formula (V), without interaction with the cytochrome P450 enzyme system. Therefore, there is less risk of drug interactions.

compared to dabigatran and melagatran; and a single oral dose of 10 mg/kg of the compounds of formula (I) (compounds 1, 2, 6, 8, 10, 12, 17, and 19) also had significant antithrombotic effect with similar efficacy to a single injection of equivalent dose of Compound (V) or dabigatran.

In particular, some of the advantages of compounds of the present invention include the following pharmacokinetic properties:

1. Improved absorption of the gastrointestinal tract to achieve improved bioavailability;
2. Minimized inter-individual and intra-individual differences in bioavailability by passive (constant) absorption; and
3. Prolonged duration of action of the active compound.

A further advantage of compounds of the present invention over previous compounds lies in that high local con-

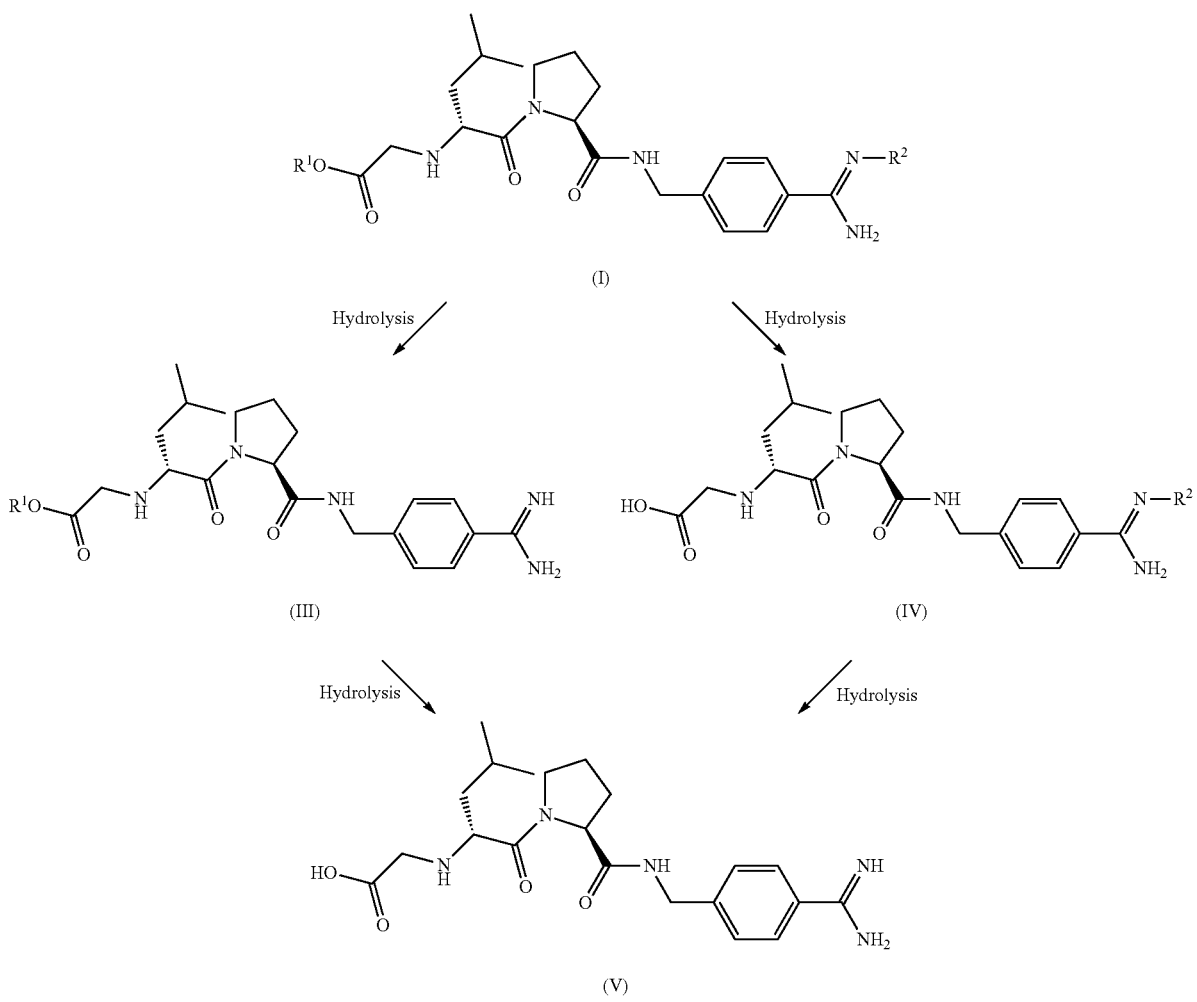

As described herein, representative compounds of formula (I) exhibit unexpectedly improved pharmacokinetic profile relative to the compound of formula (V) after oral administration and were shown to have significant oral antithrombotic efficacy. As described in Example 23 and Example 24, representative compounds of formula (I) exhibit an absolute bioavailability (calculated based on the compound of formula (V)) of at least 1.5%. Example 22 shows that a single injection of the compound of formula (V) at 10 mg/kg of provided superior anti-thrombotic activity centration of the drug would not occur off target site. Compounds of the present invention are activated through forming the compound of formula (V) after or during the gastrointestinal transit. As compounds of the present invention by themselves do not significantly inhibit serine proteases in the gastrointestinal tract, their gastrointestinal side effects can be small.

The pharmacological tests shown herein further illustrate the advantages of compounds of the present invention. Pharmacokinetic experiments in rats showed that after oral administration, only the active form of compound (V) is detected, the compound of formula (I) and other metabolites are not detected, indicating that activation of compounds of the present invention is rapid and complete.

Similarly, pharmacokinetic experiments in dogs showed that after oral administration of compounds of the present invention, no compounds of formula (I) and other metabolites were detected other than the active form of compound (V), indicating that activation of compounds of the present invention is rapid and complete. These animal experiments further demonstrate that compounds of the present invention can have good oral bioavailability.

In a rat model, a single oral administration of a compound of the invention inhibited deep vein thrombosis in rats with efficacy similar to that observed for a single injection of an equal dose of the compound of formula (V) or dabigatran. This indicates that compounds of the present invention can be orally administered to achieve antithrombotic effects, which allow optimization of the mode of administration and patient compliance.

Further, in vitro plasma stability experiments of compounds of the present invention showed that the carbamate bond in compounds of the present invention was completely cleaved within 30 min, and hydrolysis of the ester bond was also significant. Thus, the compound of formula (V) was finally produced. The compound of formula (V) was substantially stable, with no significant degradation occurred during the study period of 8 h. This rapid cleavage and hydrolysis in plasma activate the compound of formula (I) and release the active ingredient of the compound of formula (III) and formula (V). Since activation of compounds of the present invention by esterases does not involve cytochrome P450 enzymes, the risk of drug interactions can therefore be reduced.

Further, solubility tests show that compounds of the present invention have very good water solubility at acidic pH, therefore can have various advantages to the production and application of the drug. For example, it is not necessary to use complex and costly formulation techniques and allows optimization of the mode of administration (e.g., oral) and patient compliance.

EXAMPLES

The following examples describe in detail the specific synthetic methods shown in the Schemes, which were used for the synthesis of some preferable compounds of the present invention. However, it should be understood by those skilled in the art that the chemical reactions can be modified slightly for the synthesis of other thrombin inhibitors of the present invention. For example, compounds not exemplified in the present invention can also be successfully synthesized through improvement obvious to those skilled in the art. These examples are only used for illustration but are not to limit the scope of the present invention in any way.

Detection Methods

Nuclear magnetic resonance spectra are obtained using Varian INOVA-400 apparatus. Tetramethylsilane is used as the internal standard, and chemical shifts (δ) are recorded in ppm. Thin-layer chromatography (TLC, using HSG-F254 high performance silica gel prefabricated panel for the chromatography, made in Yantai Zhifu Huangwu silica gel development and pilot plant) and HPLC are used for detection of the reaction and purity of the product. Iodine vapor or irradiation with 254 A and 310 A ultraviolet lamp or 1% ninhydrin solution in ethanol is used for color development for visualization. Unless specially stated, all the reagents used are analytically pure, and anhydrous solvent and reagents are treated according to conventional methods. Melting points are determined by micrographic melting point apparatus, and the thermometer used is non-corrected.

HPLC: Agilent 1100; detection wavelength: 220 and 254 nM; column temperature: 50° C.;

Mobile Phase 1: A: 0.1% trifluoroacetic acid aqueous solution B: acetonitrile;

Method 1: Chromatographic column: Sunfire C18 (4.6× 50 mm, 3.5 μm); flow rate: 2 ml/min; mobile phase A from 95% to 5%, gradient elution for 3 minutes;

Method 2: Chromatographic column: XDB C18 (4.6×150 mm, 5 μm); flow rate: 1.5 ml/min; mobile phase A from 95% to 5%, gradient elution for 10 minutes.

Example 1 Synthesis of N-[(ethoxy)carbonyl]methyl-D-leucyl-L-prolyl-{4-[N'-(((5-methyl-2-oxo-1,3-dioxol-4-yl) methyl) oxycarbonyl) carbamimidoyl] benzyl} amide hydrochloride (Compound 1)

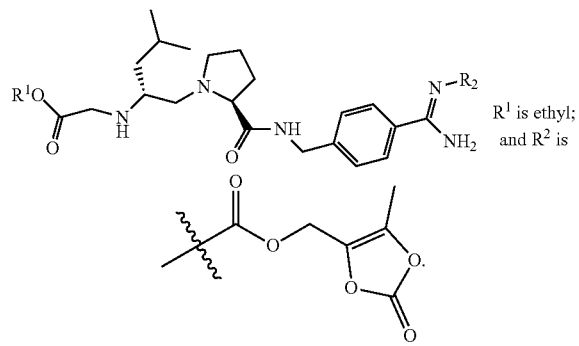

a) Preparation of N-[(ethoxy)carbonyl]methyl-N-(tert-butyloxycarbonyl)-D-leucyl-L-prolyl-{4-[(N-((benzyloxy) carbonyl) carbamimidoyl] benzyl} amide N-(2-ethoxy-oxoethyl)-N-(tert-butyloxycarbonyl)-D-Leucine (31.7 g), L-prolyl-{4-[(N-((benzyloxy) carbonyl) carbamimidoyl]benzyl}amide hydrochloride (41.6 g) and DIEA (38.8 g) were dissolved in anhydrous DMF (200 ml), and cooled down to 0° C. under the protection of nitrogen, and then HOBt (13.5 g) and EDCI (26.8 g) were added. The resulting mixture was stirred at 0° C. for 20 min and then allowed to warm up to room temperature. The reaction mixture was then stirred at room temperature for 12 hours. After which, the reaction mixture was added dropwise into water (2 L) in ice bath, and then stirred at room temperature for 15 hours. The resulting slurry was filtered and dried to give a white powder (58.4 g, yield: 86%).

HPLC method 1, MS: 680 (M+H).

b) Preparation of N-[(ethoxy)carbonyl]methyl-N-(tert-butyloxycarbonyl)-D-leucyl-L-prolyl-[(4-carbamimidoyl)benzyl]amide N-[(ethoxy)carbonyl]methyl-N-(tert-butyloxycarbonyl)-D-leucyl-L-prolyl-{4-[(N-((benzyloxy) carbonyl) carbamimidoyl]benzyl}amide (9 g) was dissolved in ethanol (100 ml), and 10% palladium-carbon (1 g) was added, and the resulting mixture aerated with hydrogen was allowed to react for 8 h at 40° C. The slurry was filtered over a pad of diatomaceous earth and evaporation of the solvent yielded a grayish black foam-like solid (7.22 g, yield: nearly quantitative).

HPLC method 1, MS: 546 (M+H)

c) Preparation of N-[(ethoxy)carbonyl]methyl-N-(tert-butyloxycarbonyl)-D-leucyl-L-prolyl-{4-[N'-(((5-methyl-2-oxo-1,3-dioxol-4-yl) methyl) oxycarbonyl)carbamimidoyl]benzyl}amide N-[(ethoxy)carbonyl]methyl-N-(tert-butyloxycarbonyl)-D-leucyl-L-prolyl-[(4-carbamimidoyl)benzyl]amide (2.7 g), DIEA (700 mg) and DMAP (50 mg) were dissolved in THF (20 ml), cooled down to 0° C., and (5-methyl-2-oxo-1,3-dioxol-4-yl)methyl (4-nitrophenyl) carbonate (1.77 g) was added dropwisely. After addition, the resulting mixture was allowed to react at 0° C. for 2 hours, and then concentrated under reduced pressure to remove the solvent. The crude product obtained was purified by column chromatography to give a colorless foam-like solid (1.73 g, yield: 49.3%).

HPLC method 2, MS: 702 (M+H).

d) Preparation of N-[(ethoxy)carbonyl]methyl-D-leucyl-L-prolyl-{4-[N'-(((5-methyl-2-oxo-1,3-dioxol-4-yl) methyl) oxycarbonyl)carbamimidoyl] benzyl}amide hydrochloride The product obtained in the above step was dissolved in ethanol (5 ml), cooled with an ice bath, and then 4M HCl/methanol solution (10 ml) was added. The resulting mixture was allowed to react under ice bath for 4 hours. The solution was filtered and concentrated in vacuo to partially remove the solvent, ether (50 ml) was added, and then the resulting slurry material was filtered and dried to give a white solid (1.4 g, yield: 82.8%)

HPLC method 2, MS: 602 (M+H).

Example 2 Synthesis of N-[(ethoxy)carbonyl] methyl-D-leucyl-L-prolyl-{4-[N'-((2-(methoxy) ethoxy)carbonyl) carbamimidoyl] benzyl}amide hydrochloride (Compound 2)

Following the method as described in Example 1, 2 g of the title compound was prepared as white solid from N-[(ethoxy)carbonyl]methyl-N-(tert-butyloxycarbonyl)-D-leucyl-L-prolyl-[(4-carbamimidoyl)benzyl]amide, yield: 68.5%.

HPLC method 2, MS: 548 (M+H).

Example 3 Synthesis of N-[(ethoxy)carbonyl] methyl-D-leucyl-L-prolyl-{4-[N'((2-(tert-butoxy) ethoxy) carbonyl) carbamimidoyl] benzyl} amide hydrochloride (Compound 3)

Following the method as described in Example 1, 1.23 g of the title compound was prepared as white solid from N-[(ethoxy)carbonyl]methyl-N-(tert-butyloxycarbonyl)-D-leucyl-L-prolyl-[(4-carbamimidoyl)benzyl]amide, yield: 39.3%.

HPLC method 2, MS: 590 (M+H).

Example 4 Synthesis of N-[(ethoxy)carbonyl] methyl-D-leucyl-L-prolyl-{4-[N'-((2-(hexyloxy) ethoxy)carbonyl) carbamimidoyl] benzyl} amide hydrochloride (Compound 4)

Following the method as described in Example 1, 0.88 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 26.9%.

HPLC method 2, MS: 618 (M+H).

Example 5 Synthesis of N-[(ethoxy)carbonyl] methyl-D-leucyl-L-prolyl-{4-[N'-((2-(2-(hydroxy) ethoxy) ethoxy) carbonyl) carbamimidoyl] benzyl} amide hydrochloride (Compound 5)

Following the method as described in Example 1, 0.66 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 21.5%.

HPLC method 2, MS: 578 (M+H).

Example 6 Synthesis of N-[(ethoxy)carbonyl] methyl-D-leucyl-L-prolyl-{4-[N'-((2-(2-(ethoxy) ethoxy) ethoxy) carbonyl) carbamimidoyl] benzyl} amide hydrochloride (Compound 6)

Following the method as described in Example 1, 2.2 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 68.5%.

HPLC method 2, MS: 606 (M+H).

Example 7 Synthesis of N-[(ethoxy)carbonyl] methyl-D-leucyl-L-prolyl-{4-[N'-((2-(2-(phenoxy) ethoxy) ethoxy) carbonyl) carbamimidoyl] benzyl} amide hydrochloride (Compound 7)

Following the method as described in Example 1, 1.9 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 55%.

HPLC method 2, MS: 654 (M+H).

Example 8 Synthesis of N-[(ethoxy)carbonyl] methyl-D-leucyl-L-prolyl-{4-[N'-((2-(2-(benzyloxy) ethoxy) ethoxy) carbonyl) carbamimidoyl] benzyl} amide hydrochloride (Compound 8)

Following the method as described in Example 1, 2.4 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 68.1%.

HPLC method 2, MS: 668 (M+H).

Example 9 Synthesis of N-[(ethoxy)carbonyl] methyl-D-leucyl-L-prolyl-{4-[N'-(2, 5, 8, 11-tetraoxatridecanoyl) carbamimidoyl] benzyl}amide hydrochloride (Compound 9)

Following the method as described in Example 1, 3.3 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 80.1%.

HPLC method 2, MS: 650 (M+H).

Example 10 Synthesis of N-[(ethoxy)carbonyl] methyl-D-leucyl-L-prolyl-{4-[N'-((3-(ethoxy) propoxy) carbonyl) carbamimidoyl] benzyl} amide hydrochloride (Compound 10)

Following the method as described in Example 1, 3.2 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 65.3%.

HPLC method 2, MS: 576 (M+H).
$^1$H NMR ((400 MHz, CDCl$_3$) δ 0.995 (t, 6H), 1.200~1.271 (m, 6H), 1.655~1.764 (m, 2H), 2.028~2.179 (m, 7H), 3.461~3.717 (m, 9H), 4.157~4.712 (m, 7H), 7.573 (d, 2H), 7.951 (s, 2H), 9.132 (s, 1H)).

Example 11 Synthesis of N-[(ethoxy)carbonyl] methyl-D-leucyl-L-prolyl-{4-[N'-((2-(ethoxycarbonyl) ethyl) carbonyl) carbamimidoyl] benzyl} amide hydrochloride (Compound 11)

Following the method as described in Example 1, 1 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 32.8%.

HPLC method 2, MS: 574 (M+H).

Example 12 Synthesis of N-[(ethoxy)carbonyl] methyl-D-leucyl-L-prolyl-{4-[N'-((2-(ethoxycarbonyl) propyl) carbonyl) carbamimidoyl] benzyl} amide hydrochloride (Compound 12)

Following the method as described in Example 1, 0.95 g of the title compound as white solid was prepared from N-[(ethoxy)carbonyl]methyl-N-(tert-butyloxycarbonyl)-D-leucyl-L-prolyl-[(4-carbamimidoyl)benzyl]amide, yield: 30.4%.

HPLC method 2, MS: 588 (M+H).

Example 13 Synthesis of N-[(ethoxy)carbonyl] methyl-D-leucyl-L-prolyl-{4-[N'-(ethoxycarbonyl) carbamimidoyl] benzyl} amide hydrochloride (Compound 13)

a) Preparation of N-(tert-butyloxycarbonyl)-D-leucyl-L-prolyl-{4-[(N-(benzyloxy) carbonyl) carbamimidoyl] benzyl} amide (tert-butyloxycarbonyl)-D-Leucine (249 g), L-prolyl-{4-[(N-(benzyloxy) carbonyl) carbamimidoyl]benzyl}amide hydrochloride (416 g) and DIEA (181 g) were dissolved in anhydrous DMF (2 L), and cooled down to 0° C. under nitrogen, and then HOBt (148 g) and EDCI (268 g) were added. The resulting mixture was stirred at 0° C. for 20 min and allowed to warm up to room temperature. The reaction was continued at room temperature for 12 hours. The reaction mixture was added dropwise into water (10 L) in ice bath, and then stirred under room temperature for 15 hours. The resulting slurry material was filtered and dried to give a white powder (551 g, yield: 93%).

HPLC method 1, MS: 594 (M+H).

b) Preparation of N-(tert-butyloxycarbonyl)-D-leucyl-L-prolyl-[(4-carbamimidoyl)benzyl]amide N-(tert-butyloxycarbonyl)-D-leucyl-L-prolyl-{4-[(N-(benzyloxy) carbonyl) carbamimidoyl] benzyl} amide (60 g) was suspended in ethanol (500 ml), and 10% palladium-carbon (6 g) was added, and the resulting mixture aerated with hydrogen was allowed to react for 8 h at 30° C. The slurry was filtered and evaporation of the solvent yielded a grayish black foam-like solid (48 g, yield: nearly quantitative)

HPLC method 1, MS: 460 (M+H).

c) Preparation of N-(tert-butyloxycarbonyl)-D-leucyl-L-prolyl-{4-[N'-(ethoxycarbonyl) carbamimidoyl] benzyl} amide N-(tert-butyloxycarbonyl)-D-leucyl-L-prolyl-[(4-carbamimidoyl) benzyl]amide (2.29 g), and DIEA (700 mg) were dissolved in THF (20 ml), cooled down to 0° C., and ethyl chloroformate (596 mg) was added dropwise slowly. After addition, the resulting mixture was allowed to react at 0° C. for 2 hours, and then concentrated under reduced pressure to remove solvent. The crude product obtained was dissolved in ethyl acetate (25 ml), passed through a FLASH column, and the resulted solution was used directly for the next step.

HPLC method 1, MS: 432 (M+H).

d) Preparation of D-leucyl-L-prolyl-{4-[N'-(ethoxycarbonyl) carbamimidoyl]benzyl} amide To the solution obtained in the above step was added ethanol (2 ml), cooled with ice bath, and then methanesulfonic acid (2.4 g) was added, the resulting mixture was allowed to react under room temperature for 8 hours. After the completion of reaction, potassium carbonate (4.1 g) solution was added dropwise slowly at 10° C., then kept stirring for 0.5 hours, the organic phase was washed with saturated salt solution and was used directly for the next step.

e) Preparation of N-[(ethoxy)carbonyl]methyl-D-leucyl-L-prolyl-{4-[N'-(ethoxycarbonyl) carbamimidoyl]benzyl} amide hydrochloride To the product obtained in the above step was added DIEA (464 mg) and ethyl bromoacetate (680 mg), the resulting mixture was stirred at 50° C. for 8 hours, After the completion of the reaction, the crude product was purified with column chromatography and then acidified with HCl to give a white solid (2 g, yield: 72.2%).

HPLC method 1, MS: 518 (M+H).

Example 14 Synthesis of N-[(ethoxy)carbonyl] methyl-D-leucyl-L-prolyl-{4-[N'-(propoxycarbonyl) carbamimidoyl] benzyl} amide hydrochloride (Compound 14)

Following the method as described in Example 13, 1.6 g of the title compound as white solid was prepared from N-(tert-butyloxycarbonyl)-D-leucyl-L-prolyl-[(4-carbamimidoyl)benzyl]amide, yield: 56.3%.

HPLC method 1, MS: 532 (M+H).

Example 15 Synthesis of N-[(ethoxy)carbonyl] methyl-D-leucyl-L-prolyl-{4-[N'-(isopropoxycarbonyl) carbamimidoyl]benzyl} amide hydrochloride (Compound 15)

Following the method as described in Example 13, 1.1 g of the title compound as white solid was prepared from N-(tert-butyloxycarbonyl)-D-leucyl-L-prolyl-[(4-carbamimidoyl)benzyl]amide, yield: 38.7%.

HPLC method 1, MS: 532 (M+H).

Example 16 Synthesis of N-[(ethoxy)carbonyl] methyl-D-leucyl-L-prolyl-{4-[N'-(butoxycarbonyl) carbamimidoyl]benzyl} amide hydrochloride (Compound 16)

Following the method as described in Example 13, 0.9 g of the title compound as white solid was prepared from N-(tert-butyloxycarbonyl)-D-leucyl-L-prolyl-[(4-carbamimidoyl)benzyl]amide, yield: 30.9%.

HPLC method 1, MS: 546 (M+H).

Example 17 Synthesis of N-[(ethoxy)carbonyl] methyl-D-leucyl-L-prolyl-{4-[N'-(hexyloxycarbonyl) carbamimidoyl]benzyl} amide hydrochloride (Compound 17)

Following the method as described in Example 13, 1.8 g of the title compound as white solid was prepared from N-(tert-butyloxycarbonyl)-D-leucyl-L-prolyl-[(4-carbamimidoyl)benzyl]amide, yield: 59%.

HPLC method 1, MS: 574 (M+H).

$^1$H NMR ((400 MHz, CDCl$_3$) δ 0.892 (t, J=6.8, 6.4 Hz, 3H), 0.935 (d, 6H), 1.179 (t, J=6.8, 7.2 Hz, 3H), 1.241~1.328 (m, 5H), 1.374~1.471 (m, 3H), 1.717 (quint, 2H), 1.859~2.085 (m, 3.5H), 2.342~2.370 (m, 1.5H), 3.263 (s, 2H), 3.405~3.470 (m, 2H), 3.613~3.658 (m, 1H), 3.996 (q, J=7.2 Hz, 2H), 4.111~4.151 (m, 2H), 4.330~4.563 (dq, J=6.4, 71.6 Hz, 2H), 4.616 (d, J=7.6 Hz, 1H), 7.282 (d, J=8.4 Hz, 2H), 7.814 (d, J=8.4 Hz, 2H)).

Example 18 Synthesis of N-[(propoxy)carbonyl] methyl-D-leucyl-L-prolyl-{4-[N'-(hexyloxycarbonyl) carbamimidoyl]benzyl} amide hydrochloride (Compound 18)

Following the method as described in Example 13, 1.1 g of the title compound as white solid was prepared from N-(tert-butyloxycarbonyl)-D-leucyl-L-prolyl-[(4-carbamimidoyl)benzyl]amide, yield: 35%.

HPLC method 1, MS: 588 (M+H).

Example 19 Synthesis of N-[(tert-butyloxy)carbonyl]methyl-D-leucyl-L-prolyl-{4-[N'-(hexyloxycarbonyl) carbamimidoyl]benzyl} amide hydrochloride (Compound 19)

Following the method as described in Example 13, 1.4 g of the title compound as white solid was prepared from N-(tert-butyloxycarbonyl)-D-leucyl-L-prolyl-[(4-carbamimidoyl)benzyl]amide, yield: 43.9%.

HPLC method 1, MS: 602 (M+H).

Example 20 Solubility Tests at Different pH Values

Weigh proper amount of the test chemical into buffered salt solutions with different pH value (4.0, 6.3, 7.4 and 9.0), the suspension was shaken at 37° C. for 1 hour. Precipitated and undissolved residues were removed by centrifugation. The content of the supernatant was determined by HPLC to analyze the solubility of the test chemical. The results are shown below:

| compound | solubility (μM) | | | |
| --- | --- | --- | --- | --- |
|  | pH 4.0 | pH 6.3 | pH 7.4 | pH 9.0 |
| 1 | 7720 | 3986 | 613 | 196 |
| 10 | 6521 | 3353 | 495 | 119 |
| 17 | 5837 | 3721 | 693 | 147 |

Example 21 Plasma Stability

An aliquot of 1 ml of rat whole blood was mixed with 50 ul of stock solution containing the test substance in DMSO (1 mg/ml) to obtain final concentration of 50 ug/ml. The mixture was incubated at 37° C. Samples were taken at time points of 0 min, 30 min, 1 h, 2 h, 4 h and 8 h, and then added to an organic solvent to terminate the reaction. After pre-treatment each sample was analyzed by LC-MS/MS to determine the plasma concentrations of compound (III), compound (IV) and compound (V). The table below shows the hydrolysis rates of different compounds converted to compound (V) measured at 30 minutes. The hydrolysis of the carbamate bond of each compound was accomplished within 30 minutes

| compound | hydrolysis rate (%) |
| --- | --- |
| 1 | 100 |
| 2 | 89 |
| 3 | 91 |
| 4 | 93 |
| 5 | 96 |
| 6 | 100 |
| 7 | 96 |
| 8 | 100 |
| 9 | 100 |
| 10 | 100 |
| 11 | 66 |
| 12 | 57 |
| 13 | 100 |
| 14 | 100 |
| 15 | 100 |
| 16 | 100 |
| 17 | 100 |
| 18 | 83 |
| 19 | 100 |

Example 22 Venous Thrombosis in Rat

Animals: SD Rat (Weight 180~210 g, Sex Male)

Solution preparation: Weigh proper amount of the test chemical, dissolved in DMSO to give the stock solutions, serial dilution with water then provided the required concentration of administration dosage.

Experimental procedures: After 3-day adaptive breeding, male Sprague-Dawley rats were randomly divided into groups: model group, positive drug group and compound groups, with 4~6 rats in each group.

The rats in the model group were given either intravenous injection or intragastric administration with equivalent solvent, those in the positive or compound group were given either intravenous injection or intragastric administration in a dose of 10 mg/kg.

5 minutes after intravenous injection or 0.5 hour after intragastric administration, rats were anesthetized by intraperitoneal injection with 10% chloral hydrate solution, the abdomen was surgically opened by a midline incision, and the inferior venae cava was carefully exposed. The left renal vein was ligated with a silk thread to initiate thrombus formation. After 6 hours of stasis, another ligature was made at the distal side 2 cm apart from the first, thrombus formed inside the vessel was carefully removed, blotted on wet filter paper and weighed.

Single Intravenous Injection (Compared with Dabigatran):

| Group | wet weight of thrombus |
|---|---|
| Model | 22.7 ± 3.5 |
| Compound of Formula (V) | 13.3 ± 1.5 |
| Dabigatran | 15.7 ± 4.0 |

Single Intravenous Injection (Compared with Melagatran):

| Group | wet weight of thrombus |
|---|---|
| Model | 19.6 ± 3.7 |
| Compound of Formula (V) | 6.8 ± 5.0 |
| Melagatran | 7.8 ± 7.6 |

Single Oral Administration:

| Group | wet weight of thrombus |
|---|---|
| Model | 28.4 ± 7.5 |
| 1 | 10.8 ± 5.1 |
| 2 | 16.7 ± 8.0 |
| 6 | 19.7 ± 6.4 |
| 8 | 12.5 ± 3.1 |
| 10 | 14.6 ± 3.6 |
| 12 | 20.5 ± 4.7 |
| 17 | 11.0 ± 5.5 |
| 19 | 13.9 ± 6.0 |

Example 23: Pharmacokinetics in Rat

Animals: SD Rat (Weight 200~300 g, Sex Male)

Intragastric solution preparation: proper amount of the test chemical was weighed, and dissolved in DMSO to give the stock solution, which was then diluted serially with 0.5% CMC-Na solution to the required concentration of administration dosage.

IV solution preparation: proper amount of compound (V) was weighed, and dissolved in normal saline to give the stock solution, which was then diluted serially to the required concentration of administration dosage.

Experimental procedures: After 3-day adaptive breeding, male Sprague-Dawley rats were divided into groups randomly with 4 rats in each group.

Rats were orally given 10 mg/kg of the test compound via gavage for oral study or given 2 mg/kg of compound (V) via the femoral vein for intravenous (i.v.) study. Blood samples were collected from the orbitat at 15 min, 30 min, 1 h, 1.5 h, 2 h, 4 h, 6 h, 8 h, 10 h, and 24 h after dosing and were analyzed by LC-MS/MS after pretreatment.

Non-compartment model of DAS2.0 software was used for data processing to calculate the pharmacokinetic parameters including maximum plasma concentration of test compound ($C_{max}$, actual values was used), time of maximum plasma concentration ($T_{max}$, actual values was used), area under the curve ($AUC_{0-t}$, calculated by trapezoid planimetry), $AUC_{0-\infty}=AUC_{0-t}+C_t/k_e$, $C_t$: plasma concentration at the last measurable time point, $k_e$: elimination rate constant; elimination half-life $t_{1/2}=0.693/k_e$; mean residence time MRT=AUMC/AUC; clearance rate $CL/F=X_0/AUC_{0-\infty}$ ($X_0$: dosage of administration); volume of distribution $V_z=CL/k_e$.

WPS software was used to calculate the mean value, standard deviation, precision and accuracy of each sample.

Pharmacokinetic parameters of compound (V) at a single i.v. dose of 2 mg/kg are shown below:

| compound | $C_{max}$ (μg/L) | $AUC_{(0-\infty)}$ (μg/L*h) | $T_{1/2}$ (h) | $CL_{z/F}$ (L/h/kg) |
|---|---|---|---|---|
| Formula (V) | 4721 | 2962 | 5.02 | 0.696 |

Pharmacokinetic parameters of compound (I) at a single oral dose of 10 mg/kg are shown below:

| compound | $C_{max}$ (μg/L) | $AUC_{(0-\infty)}$ (μg/L*h) | $T_{max}$(h) | $T_{1/2}$(h) | F(%) |
|---|---|---|---|---|---|
| 1 | 344.4 | 647.1 | 0.5 | 1.25 | 4.36 |
| 2 | 250 | 451.7 | 0.5 | 1.33 | 3.04 |
| 3 | 462.8 | 842.4 | 0.5 | 1.96 | 5.71 |
| 6 | 121.8 | 307.9 | 1 | 1.34 | 2.08 |
| 8 | 613.6 | 1309.5 | 1 | 2.41 | 8.91 |
| 9 | 86.3 | 222.3 | 1 | 1.88 | 1.50 |
| 10 | 267 | 515.5 | 1 | 2.75 | 3.49 |
| 12 | 294.7 | 704.9 | 1.5 | 3.24 | 4.85 |
| 13 | 265.5 | 670.2 | 0.5 | 3.42 | 4.53 |
| 15 | 108.6 | 244.1 | 0.5 | 3.33 | 1.65 |
| 17 | 626 | 1424.3 | 0.5 | 4.20 | 9.6 |
| 19 | 665.1 | 1506.8 | 0.5 | 4.67 | 10.3 |

Example 24: Pharmacokinetics in Dog

Animals: Male Beagle Dog

Intragastric solution preparation: proper amount of the test chemical was weighed, and dissolved in DMSO to give the stock solution, which was then diluted serially with 0.5% CMC-Na solution to the required concentration of administration dosage.

IV solution preparation: proper amount of compound (V) was weighed, and dissolved in normal saline to give the stock solution, which was then diluted serially to the required concentration of administration dosage.

Experimental procedures: After 3-day adaptive breeding, male dogs were divided into groups randomly with 4 dogs in each group.

Dogs were orally given 5 mg/kg of the test compound via gavage for oral study or given 2 mg/kg of compound (V) via the femoral vein for intravenous (i.v.) study. Blood samples were collected at 15 min, 30 min, 1 h, 1.5 h, 2 h, 4 h, 6 h, 8 h, 10 h, and 24 h after dosing and were analyzed by LC-MS/MS after pretreatment.

Non-compartment model of DAS2.0 software was used for data processing to calculate the pharmacokinetic parameters including maximum plasma concentration of test compound ($C_{max}$, actual values was used), time of maximum plasma concentration ($T_{max}$, actual values was used), area under the curve ($AUC_{0-t}$, calculated by trapezoid planimetry), $AUC_{0-\infty}=AUC_{0-t}+C_t/k_e$, $C_t$: plasma concentration at the last measurable time point, $k_e$: elimination rate constant; elimination half-life $t_{1/2}=0.693/k_e$; mean residence time MRT=AUMC/AUC; clearance rate $CL/F=X_0/AUC_{0-\infty}$ ($X_0$: dosage of administration); volume of distribution $V_z=CL/k_e$.

WPS software was used to calculate the mean value, standard deviation, precision and accuracy of each sample.

Pharmacokinetic parameters of compound (V) at a single i.v. dose of 2 mg/kg are shown below:

| compound | $C_{max}$ (μg/L) | $AUC_{(0-\infty)}$ (μg/L*h) | $T_{1/2}$ (h) | $CL_{z/F}$ (L/h/kg) |
|---|---|---|---|---|
| Formula (V) | 4039 | 4342 | 11.79 | 0.474 |

Pharmacokinetic parameters of compound (I) at a single oral dose of 5 mg/kg are shown below:

| compound | $C_{max}$ (μg/L) | $AUC_{(0-\infty)}$ (μg/L*h) | $T_{max}$(h) | $T_{1/2}$(h) | F(%) |
|---|---|---|---|---|---|
| 1 | 138.4 | 833.1 | 1.03 | 9.24 | 7.79 |
| 8 | 106.9 | 676.5 | 1.86 | 5.73 | 6.35 |
| 17 | 187.5 | 1047.9 | 1.38 | 8.65 | 9.85 |
| 19 | 179.6 | 968 | 1.5 | 9.55 | 9.06 |

Although the present invention has been described in terms of specific examples, it is to be understood that the invention can be further modified, and the invention is intended to include any modifications, uses, or in accordance with the present invention. It is also intended to be used within the scope of the appended claims.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A compound of Formula I selected from Compound Nos. 1-19, or a pharmaceutically acceptable salt thereof:

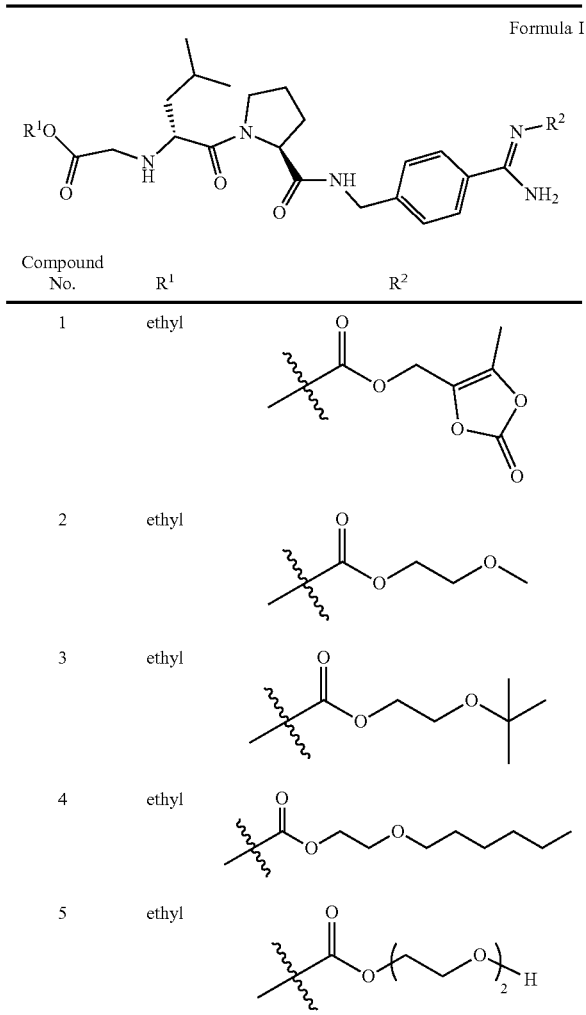

-continued

Formula I

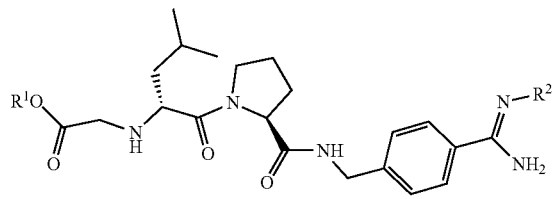

| Compound No. | R¹ | R² |
|---|---|---|
| 6 | ethyl | 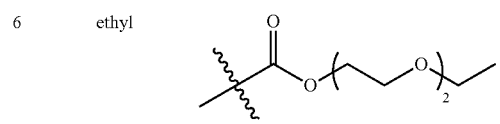 |
| 7 | ethyl | 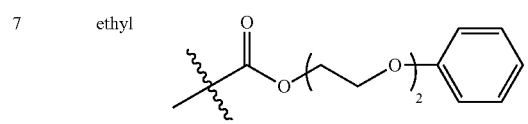 |
| 8 | ethyl | 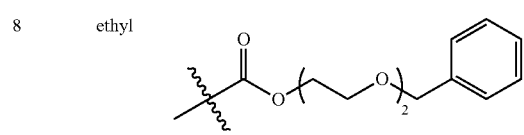 |
| 9 | ethyl | 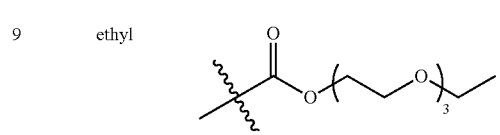 |
| 10 | ethyl | 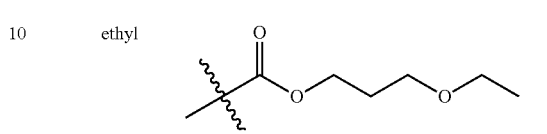 |
| 11 | ethyl | 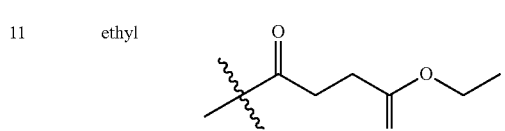 |
| 12 | ethyl | 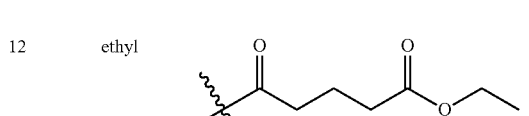 |
| 13 | ethyl |  |
| 14 | ethyl |  |

-continued

Formula I

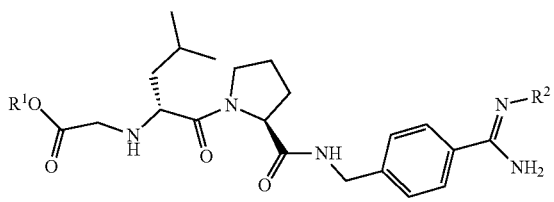

| Compound No. | R¹ | R² |
|---|---|---|
| 15 | ethyl | 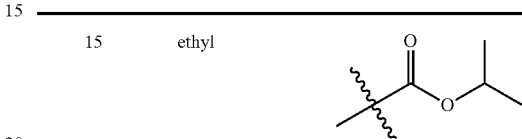 |
| 16 | ethyl | 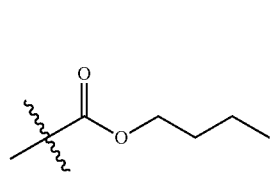 [SMILES: *C(=O)OCCCC] |
| 17 | ethyl | 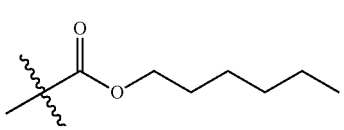 [SMILES: *C(=O)OCCCCCC] |
| 18 | n-propyl | 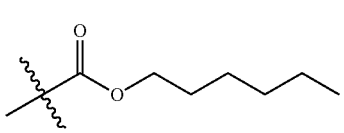 |
| 19 | tert-butyl | 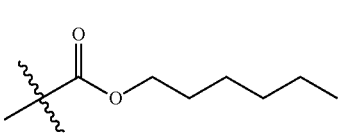 [SMILES: *C(=O)OCCCCCC] |

2. A pharmaceutical composition comprising one or more compounds of claim 1 or a pharmaceutically acceptable salt thereof, and optionally a pharmaceutically acceptable carrier.

3. The compound of claim 1, or a pharmaceutically acceptable salt thereof, wherein the compound is selected from Compound Nos. 1, 6, 8, 10, 12, 13, 17, or 19.

4. A compound or a pharmaceutically acceptable salt thereof, wherein the compound is Compound No. 17:

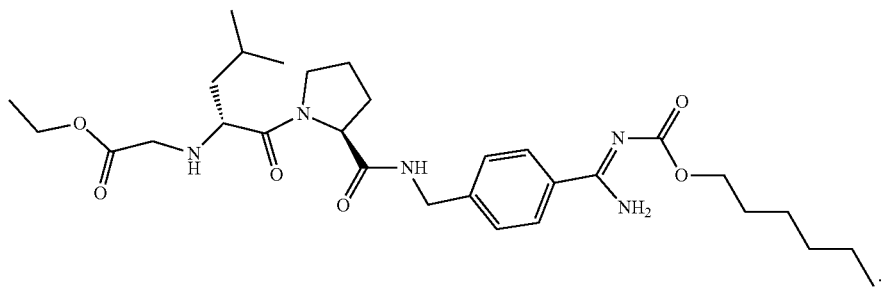
Compound No. 17
5. The compound or pharmaceutically acceptable salt thereof according to claim 4, which is a hydrochloride salt of Compound No. 17.
* * * * *